US009106057B2

(12) United States Patent
Park et al.

(10) Patent No.: US 9,106,057 B2
(45) Date of Patent: *Aug. 11, 2015

(54) WHITE-EMITTING MONOMOLECULAR COMPOUND USING EXCITED-STATE INTRAMOLECULAR PROTON TRANSFER, ORGANIC ELECTROLUMINESCENT ELEMENT AND LASER DEVICE USING THE SAME

(71) Applicants: Dongwoo Fine-Chem Co. Ltd., Jeollabuk-do (KR); SNU R&DB Foundation, Seoul (KR)

(72) Inventors: Soo Young Park, Seoul (KR); Sang Hyuk Park, Seoul (KR); Ji Eon Kwon, Seoul (KR)

(73) Assignees: DONGWOO FINE-CHEM CO. LTD., Jeollabuk-Do (KR); SNU R&DB FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/025,166

(22) Filed: Sep. 12, 2013

(65) Prior Publication Data

US 2014/0012009 A1      Jan. 9, 2014

Related U.S. Application Data

(62) Division of application No. 13/264,968, filed on Oct. 17, 2011, now Pat. No. 8,569,510.

(30) Foreign Application Priority Data

Apr. 21, 2009   (KR) .................. 10-2009-0034806
Apr. 19, 2010   (KR) .................. 10-2010-0035707

(51) Int. Cl.
| | |
|---|---|
| *H01L 51/00* | (2006.01) |
| *H01S 5/36* | (2006.01) |
| *C07D 233/60* | (2006.01) |
| *C07D 271/107* | (2006.01) |
| *C09K 11/06* | (2006.01) |
| *H05B 33/14* | (2006.01) |

(52) U.S. Cl.
CPC ............. *H01S 5/36* (2013.01); *C07D 233/60* (2013.01); *C07D 271/107* (2013.01); *C09K 11/06* (2013.01); *H01L 51/007* (2013.01); *H01L 51/0067* (2013.01); *H05B 33/14* (2013.01); *C09K 2211/1033* (2013.01); *C09K 2211/1044* (2013.01); *C09K 2211/1048* (2013.01); *C09K 2211/1092* (2013.01); *Y02B 20/181* (2013.01)

(58) Field of Classification Search
CPC ............. H01L 51/0067; H01L 51/007; C07D 271/107; C07D 233/60; H01S 5/36
USPC .......................................................... 548/145
See application file for complete search history.

(56) References Cited

U.S. PATENT DOCUMENTS

| 5,587,112 A | 12/1996 | Kauffman et al. |
|---|---|---|
| 7,262,301 B1 | 8/2007 | O'Halloran et al. |
| 2014/0012008 A1* | 1/2014 | Park et al. ................ 548/145 |

FOREIGN PATENT DOCUMENTS

| JP | 2008-64786 | 3/2008 |
|---|---|---|
| WO | 2009080797 A1 | 7/2009 |
| WO | 2010090925 A1 | 8/2010 |

OTHER PUBLICATIONS

International Search Report and Written Opinion dated Dec. 21, 2010 from International Patent Application No. PCT/KR2010/002482, filed Apr. 21, 2010.
Marcelo Comingues Kuplich, "Synthesis of New Heterocycles Benzazoles Fluorescence and its incorportion into cellulose matrix," 2007, Master's Dissertation, Universidade Federal do Rio Grande do Sul. with English Abstract.
Jangwon Seo, et al., "Highly fluorescent columnar liquid crystals with elliptical molecular shape: oblique molecular stacking and excited-state intramolecular proton-transfer fluorescence" Journal of Materials Chemistry, 2007, vol. 17, pp. 5052-5057.
Sehoon Kim, et al., "White Luminescence from Polymer Thin Films Containing Excited-State Intramolecular Proton-Transfer Dyes," Advanced Materials, 2005, vol. 17, pp. 2077-2082.
Kidwai, Mazaahir, et al., A one-pot synthesis of 1,2,4,5-tetraarylimidazoles using molecular iodine as an efficient catalyst, Mar. 22, 2006, Tetrahedron Letters 47 (2006, pp. 5029-5031.
Park, et al., A White-Light-Emitting Molecule: Frustrated Energy Transfer between Constituent Emitting Centers, J. Am. Chem. Soc., 2009, pp. 14043-14049, vol. 131 (39).
Office Action dated Jan. 15, 2013 from U.S. Appl. No. 13/264,968, filed Oct. 17, 2011.
Office Action dated Mar. 1, 2013 from U.S. Appl. No. 13/264,968, filed Oct. 17, 2011.
Office Action dated Jul. 1, 2013 from U.S. Appl. No. 13/264,968, filed Oct. 17, 2011.
Notice of Allowance dated Sep. 11, 2013 from U.S. Appl. No. 13/264,968, filed Oct. 17, 2011.

* cited by examiner

*Primary Examiner* — Yong Chu
(74) *Attorney, Agent, or Firm* — Workman Nydegger

(57) ABSTRACT

Provided are a white-emitting monomolecular compound using excited-state intramolecular proton transfer (ESIPT) characteristics, and an organic electroluminescence device and a laser device comprising same. The white-emitting monomolecular compound according to the present invention is prepared by covalently bonding at least two types of molecules which produce different colors and have excited-state intramolecular proton transfer (ESIPT) characteristics. The white-emitting monomolecular compound according to the present invention achieves white luminescence irrespective of the concentration thereof and of the state of the materials thereof, and therefore can be used in a variety of fields including an organic electroluminescence device and a laser device.

6 Claims, 8 Drawing Sheets

WHITE-EMITTING MONOMOLECULAR COMPOUND USING EXCITED-STATE INTRAMOLECULAR PROTON TRANSFER, ORGANIC ELECTROLUMINESCENT ELEMENT AND LASER DEVICE USING THE SAME

CROSS-REFERENCE TO RELATED APPLICATION

This application is a divisional, and claims the benefit, of U.S. patent application Ser. No. 13/264,968, now U.S. Pat. No. 8,569,510, entitled WHITE-EMITTING COMPOUNDS USING EXCITED-STATE INTRAMOLECULAR PROTON TRANSFER, ORGANIC ELECTROLUMINESCENT ELEMENT AND LASER MATERIAL USING THE SAME, and filed Oct. 17, 2011 (the "'968 Application") which claims priority to PCT/KR2010/002482 filed Apr. 21, 2010, which claims priority to and the benefit of Korean Patent Application No. 10-2009-0034806, filed on Apr. 21, 2009, and Korean Patent Application No. 10-2010-0035707, filed on Apr. 19, 2010. All of the aforementioned applications are incorporated herein in their respective entireties by this reference.

BACKGROUND OF THE INVENTION

1. Field of the Invention

Aspects of the present invention relate to a white-emitting monomolecular compound using excited-state intramolecular proton transfer (ESIPT), an organic electroluminescent element and a laser device using the same. More particularly, aspects of the present invention relate to a white-emitting monomolecular compound using ESIPT, which are prepared by synthesizing at least two types of compounds having ESIPT characteristics in an intramolecular state, an organic electroluminescent element and a laser device using the same.

2. Description of the Related Art

In recent years, studies for developing efficient light-emitting monomolecular compounds for a next generation flat display or white illumination light source are actively in progress. In particular, since white-emitting monomolecular compounds have various advantages, including improved stability, excellent reproducibility, and ease fabrication of devices, compared to a white luminescence system using polymeric materials or various molecular compounds, development of the white-emitting monomolecular compounds has become important more and more.

White luminescence over the entire visible area ranging from about 400 to 700 nm is generally achieved by combining two or more kinds of fluorescent or phosphorescent materials having different emission ranges.

Devices emitting substantially white light by combining two or more kinds of fluorescent or phosphorescent materials are disclosed in Korean Patent Publication No. 2003-0015870 by Eastman Kodak Company, Korean Patent Publication No. 2004-0082286 by Semiconductor Energy Laboratory K.K. of Japan, and Korean Patent Publication No. 2004-0100523 by Bistorm Co., Ltd. White-emitting monomolecular compounds which have been reported to date include "White luminescence from an assembly comprising luminescent iridium and europium complexes" by Coppo P. et al, *Angew. Chem. Int. Ed.* 46 (12), 1806-1810 (2005), and "An organic white-light emitting fluorophore" by Yang, Y., Lowry, M., Schowalter, C M., Fakayode, S. O., *J. Am. Chem. Soc.* 128, 14081-14092 (2006).

Most of the above-referenced methods utilize partial energy transfer between a higher energy band gap donor and a lower energy band gap acceptor.

According to the known methods, however, color control is quite difficult to achieve simply by mixing even a small amount of an emissive dopant with a host since light emission is easily affected by a dopant having a small band gap. This problem arises from the inter-dopant Förster-type energy transfer between the higher band gap donor and the closely located lower band gap acceptor by means of spectral matching. In addition, the energy transfer characteristics are considerably affected by the concentration and state of emitting material. Thus, if the concentration and state of the emitting material vary, color purity and stability may considerably deteriorate.

For these reasons, it has been considered that development of white-light emitting compounds is quite difficult to achieve, irrespective of the concentration or state of material.

The inventors of the present invention published a paper reporting that the use of molecules having excited-state intramolecular proton transfer (ESIPT) characteristic may restrict energy transfer between different chromophores: Sehoon Kim, Jangwon Seo, Ho Kuk Jung, Jang-Joo Kim, and Soo Young Park, "White Luminescence from Polymer Thin Films Containing Excited-State Intramolecular Proton Transfer (ESIPT) Dyes", *Adv. Mater.*, 17, 2077-2082, (2005) In the report, the inventors disclosed that a white luminescence organic electroluminescent element could be easily fabricated when ESIPT molecules having different fluorescent colors are dispersed in a monomolecular polymer.

However, since a monomolecular white emitter is not used in the method disclosed in the paper published by the present inventors, there is a problem with reproducibility of white luminescence. To solve the problem, the present inventors conducted intensive researches and discovered that the interaction between energy acceptor and donor can be completely restricted by appropriately designing and synthesizing ESIPT molecules, thereby implementing efficient white luminescence in a monomolecular state. That is to say, the present inventors developed monomolecular compounds capable of emitting white light covering the entire visible area, irrespective of the concentration and state of the compound, by newly designing and synthesizing imidazole and oxadiazole cyclic molecules containing hydroxyphenyl and hydroxynaphthyl groups of specific structures having ESIPT characteristics, thereby completing the present invention.

BRIEF SUMMARY OF THE INVENTION

Aspects of the present invention provide a white-emitting monomolecular compound capable of emitting white light using molecules having ESIPT characteristics.

Other aspects of the present invention provide an organic electroluminescent element including the white-emitting monomolecular compound.

Aspects of the present invention further provide a laser device including the white-emitting monomolecular compound.

In accordance with one aspect of the present invention, there is provided a white-emitting monomolecular compound using excited-state intramolecular proton transfer (ESIPT) characteristics, produced by covalently bonding at least two types of ESIPT molecules developing different colors.

In accordance with another aspect of the present invention, there is provided an organic electroluminescent element comprising the white-emitting monomolecular compound.

In accordance with still another aspect of the present invention, there is provided a laser device including the white-emitting monomolecular compound.

As described above, according to the present invention, white-emitting monomolecular compounds are provided by covalently bonding at least two types of ESIPT molecules. Thus, compared to the conventional white luminescence technology using a combination of two or more molecules, the luminescence monomolecular compounds according to the present invention have superior reproducibility and demonstrate stability, enhanced life characteristic, excellent quantum efficiency and a wide variety of applications irrespective of the concentration of the material or the state of the material in either a solid or liquid state.

In particular, when the white-emitting monomolecular compounds according to the present invention are used as emissive materials for an organic electroluminescent element, they have advantages, including cost reduction and simplifying of fabrication process. Additionally, the white-emitting monomolecular compounds according to the present invention may be used in various applications including organic electroluminescent elements, laser devices, UV stabilizers, chemosensors, solar concentrators, and so on.

Additional aspects and/or advantages of the invention will be set forth in part in the description which follows and, in part, will be obvious from the description, or may be learned by practice of the invention.

BRIEF DESCRIPTION OF THE DRAWINGS

The objects, features and advantages of the present invention will be more apparent from the following detailed description in conjunction with the accompanying drawings, in which.

DETAILED DESCRIPTION OF THE PREFERRED EMBODIMENTS

Hereinafter, embodiments of the present invention will be described in detail with reference to the accompanying drawings.

The present invention provides a white-emitting monomolecular compound having at least two kinds of molecules having excited-state intramolecular proton transfer (ESIPT) characteristics covalently bonded to provide different colors.

Figure 1:
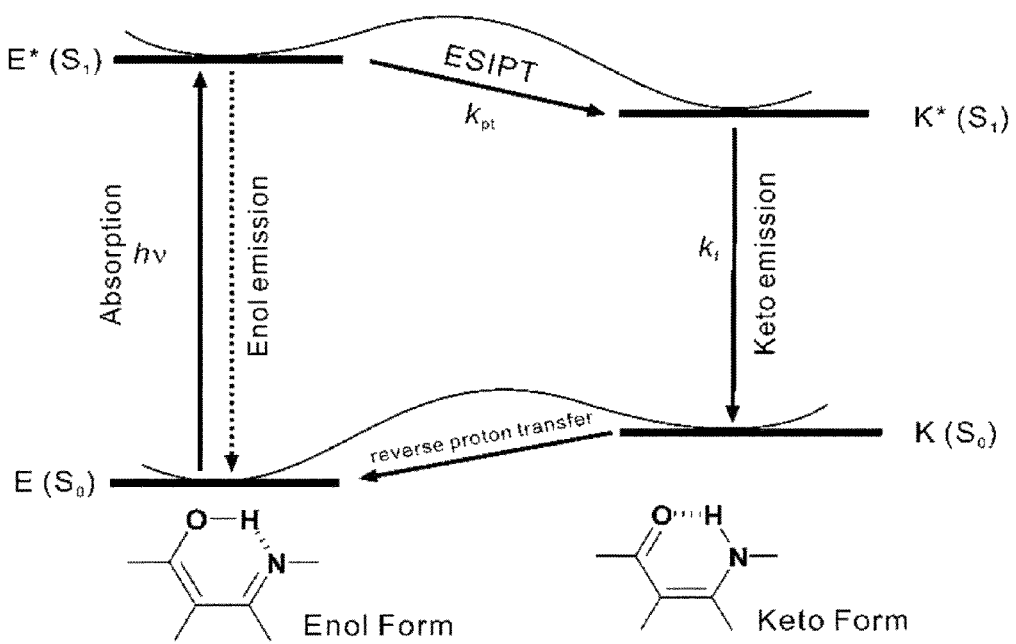
FIG. 1 is a schematic representation of the principle of color development in molecules having ESIPT characteristics.

The ESIPT is a phototautomerization in which protons are transferred in the excited states of molecules, as shown in FIG. 1. That is to say, the molecule having ESIPT having characteristics, a proton donor such as —OH, —NH, or —SH group having an intramolecular hydrogen bond and a proton acceptor such as N, O, S, or F, exists stably in the enol form when it is in the ground state and in the keto form when it is in the excited state. Thus, the ESIPT molecule usually emits light in the keto form generated after undergoing proton transfer in the excited state within a very short time (in picosecond (ps) level). Accordingly, the molecule having ESIPT having characteristics (to be briefly referred to as "ESIPT molecule") has a four-level energy structure, as shown in FIG. 1. In addition, Stokes' shift between absorption and emission energy is maximized by above-described mechanism, thereby minimizing a reduction in fluorescence due to partial overlap between absorption and luminescence. In addition, population inversion is facilitated due to four-level photophysical properties. Further, stimulated emission can be advantageously realized due to a high optical gain.

The white-emitting monomolecular compound according to the present invention may have a structure represented by Formula 1 or Formula 2:

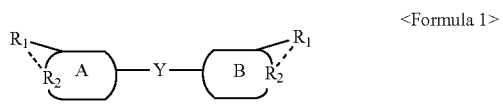

<Formula 1> wherein A and B are ESIPT molecules emitting different colors, respectively, $R_1$ and $R_2$ are functional groups having a proton donor and a proton acceptor capable of forming an intramolecular hydrogen bond, and Y indicates a covalent bond between the ESIPT molecules:

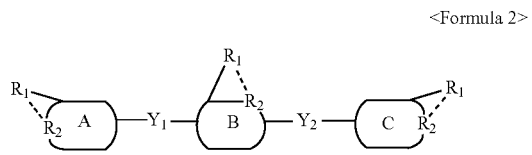

<Formula 2> wherein A, B and C are ESIPT molecules emitting different colors, respectively; $R_1$ and $R_2$ are functional groups having a proton donor and a proton acceptor capable of forming an intramolecular hydrogen bond, and $Y_1$ and $Y_2$, which may be the same or different, indicate a covalent bonds between the ESIPT molecules.

In the white-emitting monomolecular compound having Formula 1, A and B represent ESIPT molecules developing different colors, respectively, preferably ESIPT molecules developing complementary colors to achieve white luminescence by combining the colors.

Figure 2:
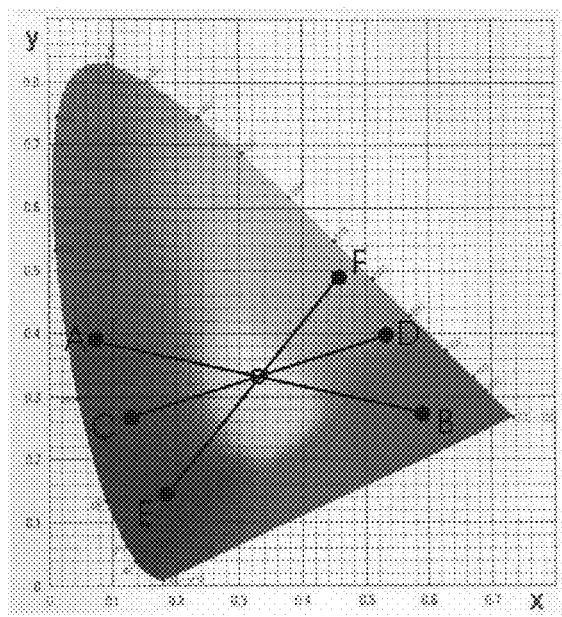
FIG. 2 illustrates the complementary color relationship in CIE 1931 coordinates.

Here, the complementary colors refer to paired colors, such as A-B, C-D, and E-F, as shown in FIG. 2, which are symmetrically positioned with respect to ideal white light (x,y)=(0.33, 0.33) on the color coordinates like CIE 1931 coordinates. White light can be generated by summing three primary colors (red, green and blue) of light. Thus, the white-emitting monomolecular compound having Formula 2 may also be achieved. That is to say, the white-emitting monomolecular compound according to the present invention may also achieve white luminescence in the form of a monomolecular compound prepared by covalently bonding three ESIPT molecules developing different colors.

In order to achieve white luminescence using a monomolecular compound by covalently bonding at least two types of molecules developing different colors, like in the present invention, it is necessary to use a system without energy transfer. In the present invention, the energy transfer can be prevented by completely restricting an interaction between an energy acceptor and an energy donor using ESIPT characteristics, thereby achieving efficient white luminescence using a monomolecular compound, which will be described in more detail with reference to FIG. 3.

Figure 3:
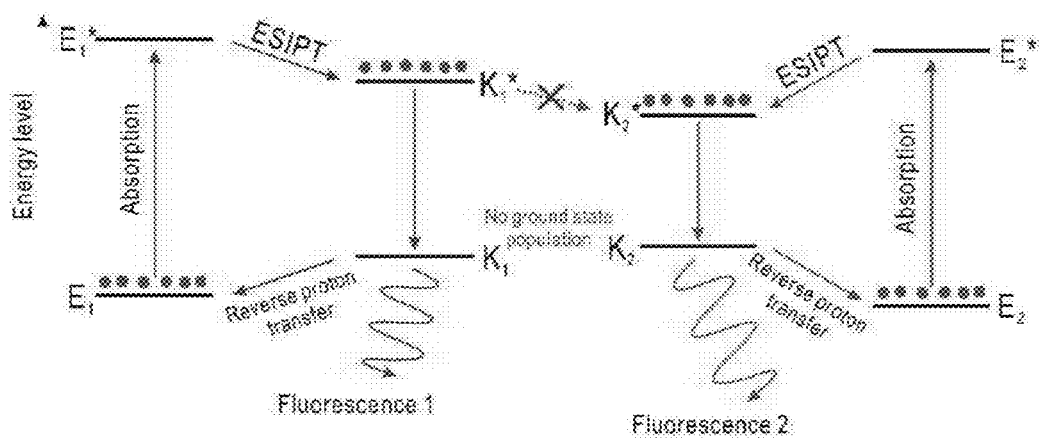
FIG. 3 is a schematic representation of the principle of white luminescence using ESIPT.

The white-emitting monomolecular compound according to the present invention is capable of preventing energy transfer due to four-level energy structures of the respective ESIPT molecules covalently bonded with each other. That is to say, as shown in FIG. 3, absorbance of an orange luminescent phosphor and absorbance of a blue luminescent phosphor occur in the same UV area. Thus, since the emission energy of the blue luminescent phosphor is not spectrally overlapped with the absorption energy of the orange luminescent phosphor, absorption-emission energy transfer or Förster resonance energy transfer does not occur.

Basically, the energy transfer occurs by an interaction between the excited state ($K_1^*$, $K_2^*$ of FIG. 3) of an energy donor and the ground state ($K_1$ and $K_2$) of an energy acceptor. However, in the white luminescent material based on ESIPT, like in the present invention, since the ground states ($K_1$, $K_2$) of the keto energy acceptor have unstable energy, they are transferred within a very short time to ground states ($E_1$ and $E_2$), respectively. Thus, there is no population of the ground states ($K_1$ and $K_2$). Therefore, the interaction between the excited state of the energy donor and the ground state of the energy acceptor can be fundamentally prevented.

Consequently, when ESIPT molecules are bonded to each other, energy transfer can be completely prevented, irrespective of the concentrations and states of materials, thereby achieving novel, efficient white-emitting monomolecular compounds.

The ESIPT molecules employed in Formulae 1 and 2 may include well known compounds. Preferably, the ESIPT molecules employed in Formulae 1 and 2 may include compounds represented by Formulae 3 to 7:

<Formula 3>

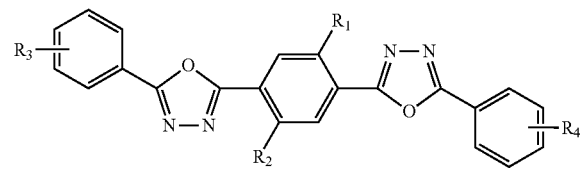

wherein $R_1$ to $R_4$ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group; and at least one of $R_1$ and $R_2$ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring <Formula 4>

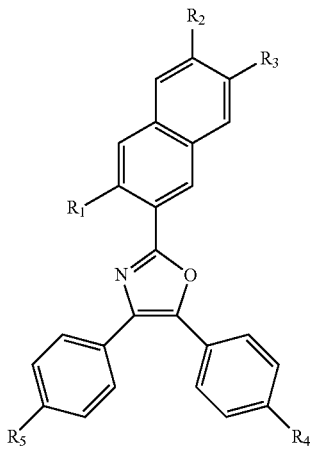

wherein $R_1$ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring; and $R_2$ to $R_5$ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group;

<Formula 5>

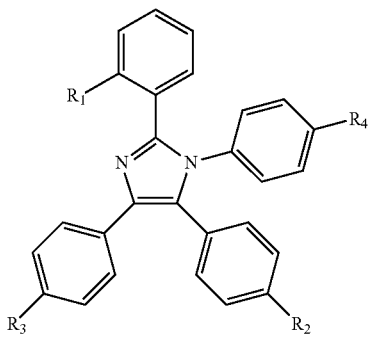

wherein R₁ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring; and R² to R₄ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group;

<Formula 6>

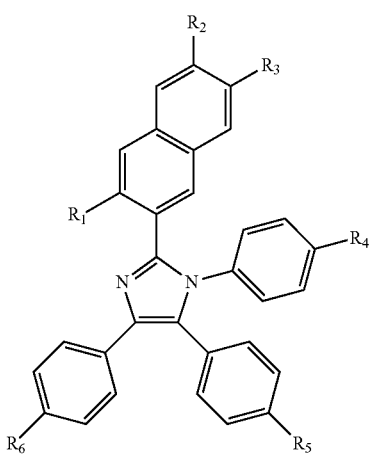

wherein R₁ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring; and R₂ to R₅ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group; and <Formula 7>

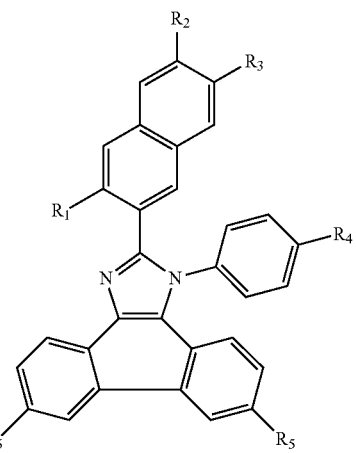

wherein R₁ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring; and R₂ to R₅ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic cyclic compound or an aryl group, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group.

In the white-emitting monomolecular compound according to the present invention, the ESIPT molecules developing different colors are linked to each other by covalent bonds. Here, the covalent bonds between the ESIPT molecules may have various structures defined by Formulae 8 to 16:

<formula 8>

<formula 9>

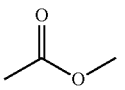

<formula 10>

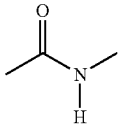

<formula 11>
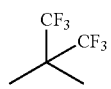

<formula 12>
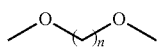

<formula 13>

<formula 14>
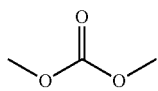

<formula 15>
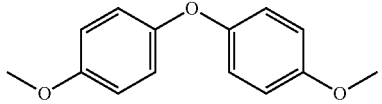

<formula 16>
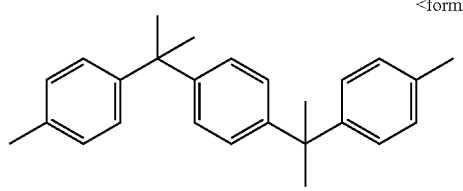

That is to say, the white-emitting monomolecular compound according to the present invention is a compound having at least two types of ESIPT molecules developing different colors, connected to each other as represented by Formulae 8 to 16, the at least two types of ESIPT molecules rendering white light by combining colors developed by the ESIPT molecules of Formulae 3 to 7.

Specific examples of the white-emitting monomolecular compound according to the present invention include the followings.

First, the white-emitting monomolecular compound represented by Formula 1 is preferably a compound of Formula 17

<Formula 17>
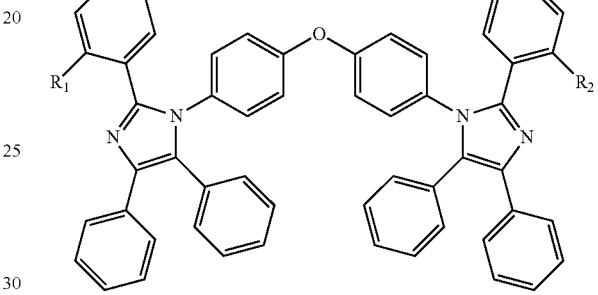

wherein $R_1$ and $R_2$ are each independently selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring.

More preferably, the compound of Formula 17 is a compound of Formula 18:

<Formula 18>
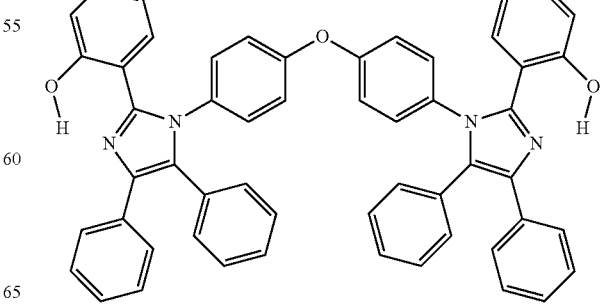

In addition, the white-emitting monomolecular compound represented by Formula 1 is preferably a compound of Formula 19:

<Formula 19>

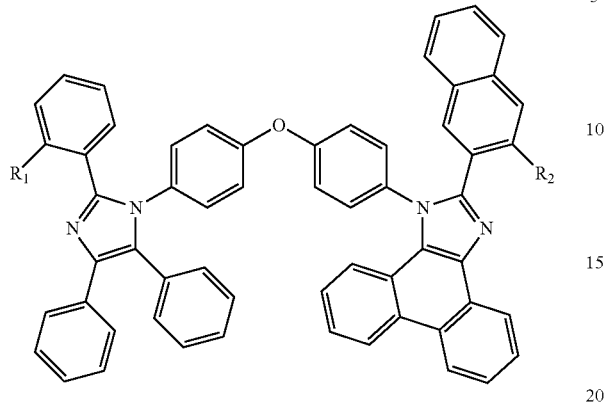

wherein $R_1$ and $R_2$ are each independently selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring.

More preferably, the compound of Formula 19 is a compound of Formula 20:

<Formula 20>

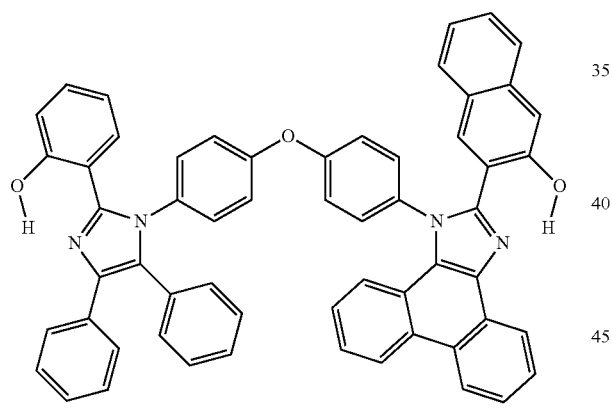

The white-emitting monomolecular compound represented by Formula 1 is preferably a compound of Formula 21:

<Formula 21>

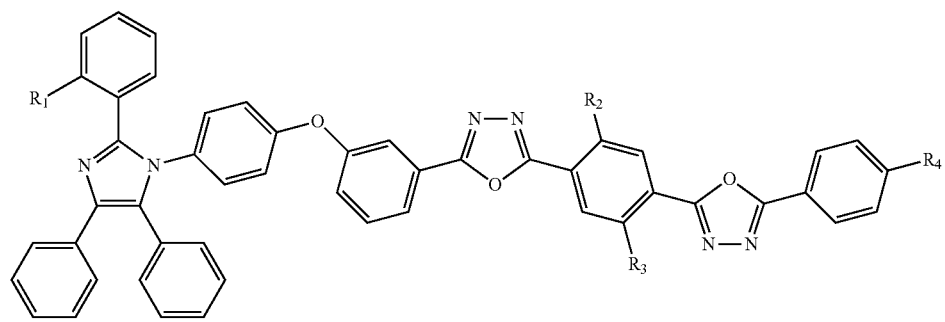

wherein $R_2$ to $R_4$ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group; and at least one of $R_1$ and $R_2$ or $R_3$ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring.

The compound of Formula 21 is preferably a compound of Formula 22:

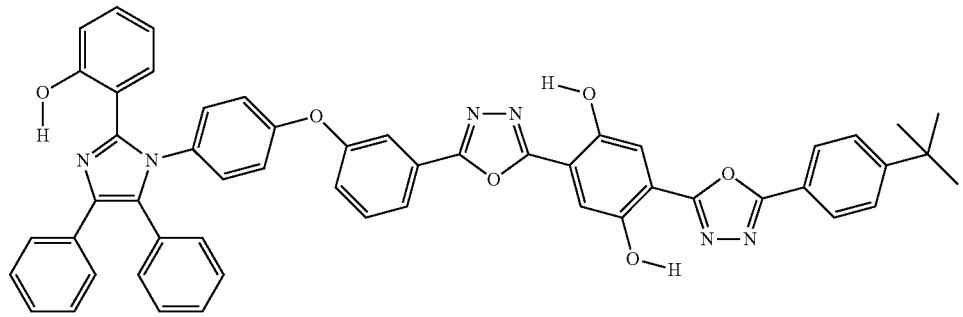

<Formula 22>

In addition, the white-emitting monomolecular compound represented by Formula 2 is preferably a compound of Formula 23:

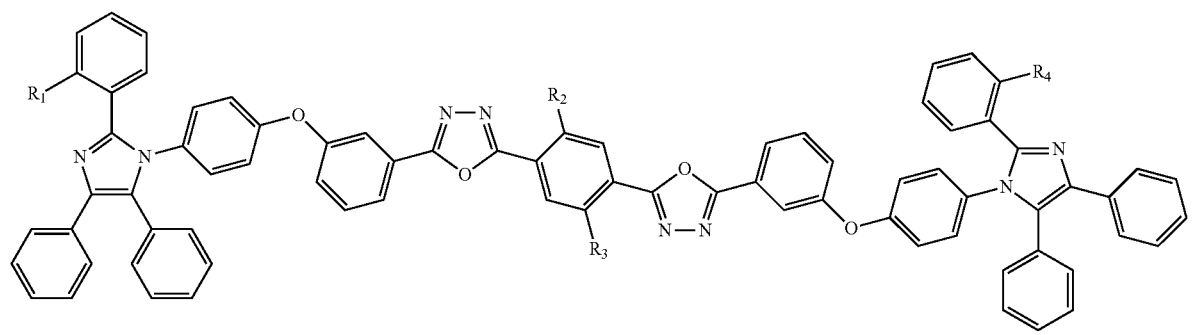

<Formula 23> wherein $R_2$ and $R_3$ are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, and a cyano group; and at least one of $R_1$, $R_2$ and $R_3$ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring.

More preferably, the compound of Formula 23 is a compound of Formula 24:

<Formula 24>

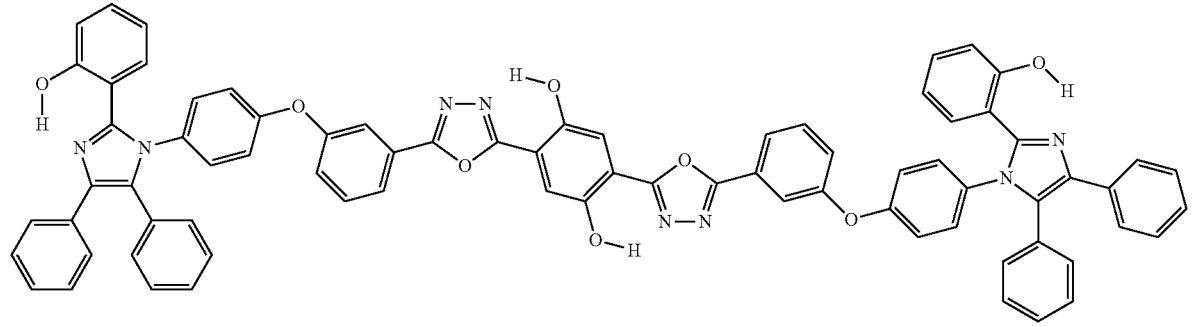

The white-emitting monomolecular compounds according to the present invention, as represented by Formulae 1 and 2, in particular, imidazole and oxadiazole cyclic compounds, are capable of achieving white luminescence while having high stability, excellent quantum efficiency, extended emissive life time characteristics, and high thermal stability.

The white-emitting monomolecular compounds can be applied to a variety of fields. For example, an emissive layer can be formed by depositing only the white-emitting monomolecular compound according to the present invention or dispersing the white-emitting monomolecular compound according to the present invention in a host material, to be used in fabricating an organic electroluminescent element. Further, the white-emitting monomolecular compounds according to the present invention may be used in various applications including organic electroluminescent elements, laser devices, UV stabilizers, chemosensors, solar concentrators, and so on.

Hereinafter, the organic electroluminescent element including the white-emitting monomolecular compound according to the present invention will be described in more detail. However, the use of the white-emitting monomolecular compounds according to the present invention is not limited to the organic electroluminescent element described below.

The white-emitting monomolecular compound according to the present invention may be used as an emissive material or a dopant.

Here, the organic electroluminescent element may have a structure that is known well in the art. For example, the organic electroluminescent element may include a positive electrode, a hole injecting layer, a hole transporting layer, an emissive layer, an electron injecting layer, an electron transporting layer, and a negative electrode, stacked on a substrate.

The white-emitting monomolecular compound according to the present invention may be included in one selected from the group consisting of the hole injecting layer, the hole transporting layer, the emissive layer, the electron injecting layer, and the electron transporting layer. Preferably, the white-emitting monomolecular compound according to the present invention may be included in the emissive layer.

The positive electrode may be formed of, for example, a metal oxide or a metal nitride, such as ITO, IZO, zinc oxide, zinc aluminum oxide or titanium nitride; a metal such as gold, platinum, silver, copper, aluminum, nickel, cobalt, lead, molybdenum, tungsten, tantalum or niobium; alloys of these metals or alloys of copper iodides; or a conductive polymer such as polyaniline, polythiophene, polypyrrole, polyphenylenevinylene, or poly(3-methylthiophene). The positive electrode may be formed of at least one selected from the above-listed materials, either alone or in mixtures of two or more materials. In addition, the positive electrode may have a multi-layered structure having multiple layers having the same composition or different compositions.

Known materials may be used as the hole injecting layer and the hole injecting layer may be formed of a material to a thickness of 5 nm-100 nm, the material including, but not limited to, PEDOT/PSS or copper phthalocyanine (CuPc), 4,4',4"-tris(3-methylphenylphenylamino)triphenylamine (m-MTDATA), and 4,4',4"-tris((N-(naphthalene-2-yl)-N-phenylamino)triphenylamine (2-TNATA).

Known materials may be used as the hole transporting layer and non-limiting examples of the hole transporting layer may include 4,4'-bis[N-(1-naphthyl)-N-phenyl-amino]-biphenyl (NPD), and N,N'-diphenyl-N,N'-bis(3-methylphenyl)-1,1'-biphenyl-4,4'-diamine (TPD).

As described above, the emissive layer preferably includes the white-emitting monomolecular compound according to the present invention. That is to say, the emissive layer may be formed by depositing one selected from the white-emitting monomolecular compounds according to the present invention or depositing together at least two types of the white-emitting monomolecular compounds according to the present invention. When necessary, the emissive layer may be formed by dispersing at least one selected from the white-emitting monomolecular compounds according to the present invention in a host material. Alternatively, a dopant material may be additionally used in forming the emissive layer.

Non-limiting examples of the host material may include (4,4'-bis(2,2-diphenyl-ethene-1-yl)diphenyl (DPVBi), bis(styryl)amines (DSA), bis(2-methyl-8-quinolinolato)(triphenylsiloxy)aluminum(III)(SAlq), bis(2-methyl-8-quinolinolato)(para-phenolato)aluminum (III) (BAlq), bis(salen) zinc (II), 1,3-bis[4-(N,N-dimethylamino)phenyl-1,3,4-oxadiazolyl]benzene (OXD8), 3-(biphenyl-4-yl)-5-(4-dimethylamino)-4-(4-ethylphenyl)-1,2,4-triazole (p-EtTAZ), 3-(4-biphenyl)-4-phenyl-5-(4-tertiary-butylphenyl)-1,2,4-triazole (TAZ), 2,2',7,7'-tetrakis(biphenyl-4-yl)-9,9'-spirofluorene (Spiro-DPVBI), tris(para-tertiary-phenyl-4-yl)amine (p-TTA), 5,5-bis(dimethylboryl)-2,2-bithiophene (BMB-2T) and perylene.

In addition, usable examples of host or dopant materials may include tris(8-quinolato)aluminum (III) (Alq3), DCM1 (4-dicyanomethylene-2-methyl-6-(para-dimethylaminostyryl)-4H-pyran), DCM2(4-dicyanomethylene-2-methyl-6-(zulolidine-4-yl-vinyl)-4H-pyran), DCJT (4-

(dicyanomethylene)-2-methyl-6-(1,1,7,7-tetramethylzulolidyl-9-enyl)-4H-pyran), DCJTB (4-(dicyanomethylene)-2-tertiary butyl-6-(1,1,7,7-tetramethylzulolidyl-9-enyl)-4H-pyran), DCJTI (4-dicyanomethylene)-2-isopropyl-6-(1,1,7,7-tetramethyl-zulolidyl-9-enyl)-4H-pyran), Nile red, and Rubrene.

The electron transporting layer materials are known in the related art and examples of materials that may be suitable for the electron transporting layer may include aryl-substituted oxadiazole, aryl-substituted triazole, aryl-substituted phenanthroline, benzoxazole, and benzothiazole compounds.

Specific examples of the electron transporting layer compound may include 1,3-bis(N,N-t-butyl-phenyl)-1,3,4-oxadiazole (OXD-7), 3-phenyl-4-(1'-naphthyl)-5-phenyl-1,2,4-triazole (TAZ), 2,9-dimethyl-4,7-diphenyl-phenanthroline ("BCP"), bis(2-(2-hydroxyphenyl)-benzoxazolate)zinc, and bis(2-(2-hydroxyphenyl)-benzothiazolate)zinc. Other electron transporting layer materials may include (4-biphenyl)(4-t-butylphenyl) oxidiazole (PDB), and tris(8-quinolato)aluminum (III) (Alq3).

Known materials may be used as materials of the electron injecting layer and the negative electrode. For example, LiF may be used as the electron injecting layer, but not limited thereto, and a metal having a low work function, such as Al, Ca, Mg, or Ag, may be used as a material of the negative electrode. Aluminum (Al) is preferably used as the material of the negative electrode.

The organic electroluminescent element according to the present invention may be applied to various kinds of display devices. For example, the organic electroluminescent element may be used as a light source of a backlight unit, or an independent light source. The display devices may be ones using a backlight unit, for example, an organic light-emitting diode (OLED).

Hereinafter, a laser device using the white-emitting monomolecular compound according to the present invention will be described in more detail. However, the use of the white-emitting monomolecular compound according to the present invention is not limited to the laser device described below.

In general, ESIPT molecules have their own four-level systems. In particular, the ESIPT molecules easily undergo population inversion when they exist in keto forms. Thus, the ESIPT molecules have a high optical gain due to pumping using laser. Therefore, the white-emitting monomolecular compound according to the present invention may also be useful for the laser device.

For example, the compound of Formula 18 is allowed to grow into a single crystalline material in the presence of ethylacetate, followed by pumping using a 355 nm Nd:YAG laser. Here, pulse-excited emission spectra were measured by using an actively/passively mode-locked Nd:YAG Laser (Quantel, YG701). As a result, amplified spontaneous emission (ASE), also known as mirrorless lasing, was easily observed.

The present invention will now be described in greater detail with reference to the following examples. The following examples are for illustrative purposes only and are not intended to limit the scope of the invention.

Synthesis Example

In order to efficiently cover the visible light area ranging from 400 nm to 700 nm, 2-(1,4,5-triphenyl-1H-imidazole-2-yl)phenol (HPI, $\lambda_{max}$=460 nm), 2,5-bis(5-(4-tert-butylphenyl)-1,3,4-oxadiazole-2-yl)benzene-1,4-diol (DOX, $\lambda_{max}$=580 nm), 3-(1,4,5-triphenyl-1H-imidazole-2-yl)naphthalene-2-ol (HPNI, $\lambda_{max}$=580 nm) were selected from ESIPT molecules having emission wavelengths of complementary colors for blue and orange, and the white-emitting monomolecular compounds of Formulae 18, 20, 22 and 24, including the selected molecules or combinations thereof, were synthesized.

Synthesis Example 1

3-(4-nitrophenoxy)benzoic acid 7.52 ml of fluoro-4-nitrobenzene (70.8 mmol) and 9.79 g of 3-hydroxybenzoic acid (70.8 mmol) were dissolved in 150 ml of DMSO at room temperature, 21 g of potassium carbonate (151.9 mmol) was added thereto, heated to 130□, and then reacted for 12 hours. The reactant solution was poured into excess water, neutralized with hydrochloric acid, filtered, and dried to yield a product having Formula 25 as a white powder (18.7 g, Yield 98%). $^1$H NMR (300 MHz, CDCl$_3$) analytical results of the product were as follows:

$^1$HNMR (300 MHz, CDCl$_3$): □ [ppm] 7.03 (d, 2H), 7.33 (d, 1H), 7.54 (t, 1H), 7.80 (s, 1H), 7.98 (d, 1H), 8.22 (d, 2H), 12.70 (s, 1H)

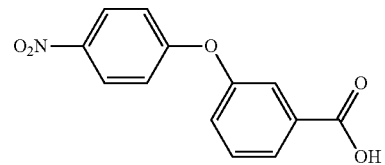

<Formula 25>

Synthesis Example 2 ethyl3-(4-nitrophenoxy)benzoate 18 g of 3-(4-nitrophenoxy)benzoic acid (69.4 mmol) prepared in Synthesis Example 1 was dissolved in 120 ml of ethanol, 35 ml of hydrochloric acid (10N) was added thereto, heated to HOD and then reacted for 12 hours. The reactant solution was poured into excess water, neutralized with a 1N aqueous solution of sodium chloride, filtered, and dried with magnesium sulfate, followed by removing ethylacetate, to yield a tacky product having Formula 26 (19 g (~65 mmol), Yield 95%). $^1$H NMR (300 MHz, CDCl$_3$) analytical results of the product were as follows:

$^1$H NMR (300 MHz, CDCl$_3$): □ [ppm] 1.28 (s, 3H), 4.30 (t, 2H), 7.20 (d, 2H), 7.35 (d, 1H), 7.73 (s, 1H), 7.82 (t, 1H), 7.78 (d, 1H), 8.22 (d, 2H).

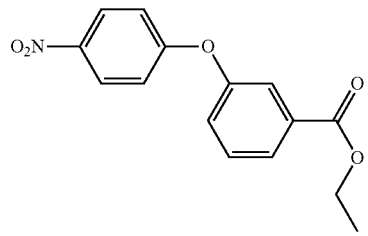

<Formula 26>

Synthesis Example 3

3-(4-nitrophenoxy)benzohydrazide 19 g of ethyl3-(4-nitrophenoxy)benzoate prepared in Synthesis Example 2 was dissolved in 200 ml of ethanol, 35 ml of hydrazine monohydrate was added thereto, and reacted under reflux for 24 hours. The reactant solution was poured into excess water and neutralized with 1N hydrochloric acid, and recrystallized with an ethylacetate solution to yield a product having Formula 27 (15.3 g, Yield 85%). $^1$H NMR (300 MHz, CDCl$_3$) analytical results of the product were as follows:

$^1$H NMR (300 MHz, CDCl$_3$): □ [ppm] 1.36 (m, 3H), □ 4.10 (s, 2H), 7.03 (d, 2H), 7.39 (d, 1H), 7.73 (s, 1H), 7.75 (d, 1H), 7.90 (t, 1H), 8.20 (d, 2H).

<Formula 27>

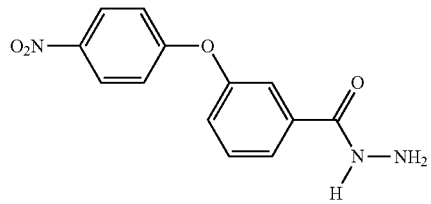

Synthesis Example 4

4-t-butylbenzohydrazide 5.2 g of 4-t-butylbenzoic acid (29.2 mmol) was dissolved in 15 ml of thionylchloride (206.5 mmol) at room temperature, and a small amount of N-dimethylformamide (DMF) was added thereto, heated to 80□ and then reacted for 8 hours. The crude product was cooled to room temperture, and filtered under reduced pressure for removing thionylchloride, giving a product as a powder, which is then dissolved in 120 ml of THF, followed by adding 35 ml of hydrazine monohydrate (0.722 mol) and 3.7 ml of triethylamine (26.3 mmol) and heating at 65□ for inducing a reaction for 12 hours. After the reaction was completed, filtration under reduced pressure was carried out to remove THF and a remainder of hydrazine monohydrate. Excess water was added to the resultant product and neutralized with hydrochloric acid. After the filtration, the reactant product was recrystallized using ethylacetate to yield a product having Formula 28 as a powder (3.5 g, Yield 64%). $^1$H NMR (300 MHz, CDCl$_3$) analytical results of the product were as follows:

$^1$H NMR (300 MHz, CDCl$_3$): □ [ppm] 1.33 (s, 9H), 4.08-4.11 (m, 3H), 7.44 (d, 2H), 7.67 (d, 2H).

<Formula 28>

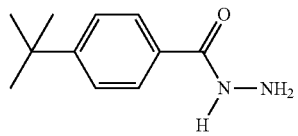

Synthesis Example 5 diethyl-2,5-bis(hexyloxy)terephthalate 5 g of diethyl-2,5-dihydroxyterephthalate (19.67 mmol) was dissolved in 100 ml of dimethylformamide (DMF) at room temperature, 10.87 g of potassium carbonate (138.21 mmol) and 16.6 ml of hexylbromide (118.02 mmol) were added thereto, and heated to 95□ for causing a reaction to take place for 12 hours, followed by performing fractional distillation for removal of DMF and a remainder of hexylbromide. Then, excess water was added to the resultant product, neutralized with hydrochloric acid, filtered, and dried under vacuum to yield a product having Formula 29 (7.9 g, Yield 95%). XH NMR (300 MHz, CDCl$_3$) analytical results of the product were as follows:

$^1$HNMR (300 MHz, CDCl$_3$): □ [ppm] 0.92 (s, 6H), 1.39 (m, 16H), 1.43 (m, 6H), 4.30 (t, 4H), 4.38 (t, 4H), 7.85 (s, 2H).

<Formula 29>

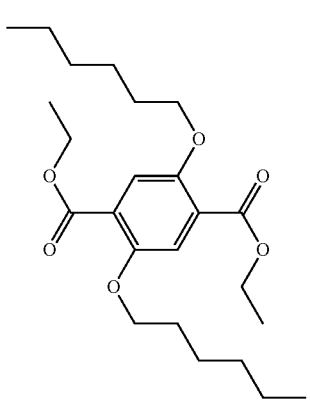

Synthesis Example 6

2,5-bis(hexyloxy)terephthalate 7.9 g of diethyl 2,5-dihydroxyterephthalate prepared in Synthesis Example 5 was dissolved in 150 ml of ethanol at room temperature, and a small amount of potassim hydroxide was added thereto. Then, the reaction mixture was reacted for 12 hours under reflux. The crude product was cooled to room temperture, distilled under reduced pressure for removing the solvent, followed by adding excess water and hydrochoric acid to adjust the pH level of the reactant solution to pH 4. The resultant product was filtered and dried under vacuum to yield 5.0 g of a product having Formula 30. $^1$H NMR (300 MHz, CDCl$_3$) analytical results of the product were as follows:

$^1$HNMR (300 MHz, CDCl$_3$): □ [ppm] 0.92 (d, 6H), 1.34-1.56 (m, 12H), 1.94 (m, 4H), 4.30 (t, 4H), 7.88 (s, 2H), 11.14 (s, 2H).

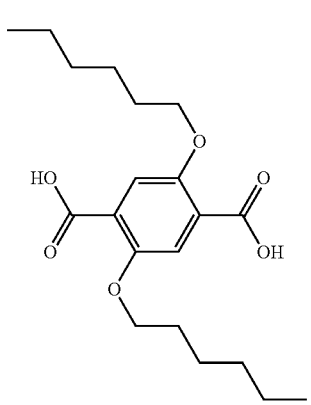

<Formula 30>

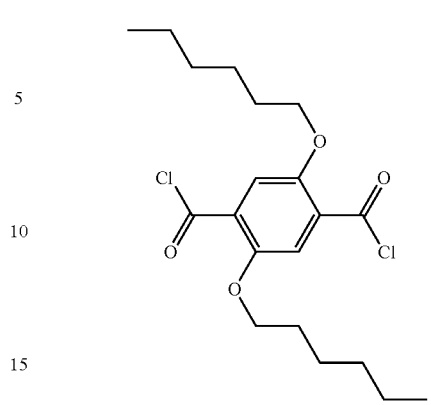

<Formula 31>

Synthesis Example 7

2,5-bis(hexyloxy)terephthaloxychrloride

1.2 g of 2,5-bis(fiexyloxy)terephtfialate (3.3 mmol) prepared in Synthesis Example 6 was dissolved in 15 ml of thionylchloride at room temperature, and a small amount of N-dimethylformamide (DMF) was added thereto, heated to 80□ and then reacted for 6 hours. The crude product was cooled to room temperture, and filtered under reduced pressure for removing thionylchloride, giving a product having Formula 31 (1.3 g, Yield 98%). $^1$H NMR (300 MHz, CDCl$_3$) analytical results of the product were as follows:

$^1$HNMR (300 MHz, CDCl$_3$): □ [ppm] 0.90 (s, 6H), 1.31-1.49 (m, 12H), 1.83 (m, 4H), 4.06 (t, 4H), 7.80 (s, 2H).

Synthesis Example 8

N'-1-(4-t-butylbenzoyl)-2,5-bis(hexyloxy)-N'-4-(3-(4-nitrophenoxy)benzoyl)terephthalohydrazide

1.32 g of 2,5-bis(hexyloxy)terephthaloyl dichloride (3.3 mmol) prepared in Synthesis Example 7 was dissolved in 60 ml of THF at room temperature, and then added thereto a solution prepared by dissolving 0.90 g of 3-(4-nitrophenoxy)benzohydrazide (3.3 mmol) prepared in Synthesis Example 3 and 0.64 g of 4-t-butylbenzohydrazide (3.3 mmol) prepared in Synthesis Example 4 in 30 ml of THF, followed by stirring for 12 hours for inducing a reaction. After the reaction was completed, the solvent THF was removed at reduced pressure, filtered and performing silica gel column chromatography (developed with a solution having ethylacetate:n-hexane mixed in a ratio of 1:3) to yield a product having Formula 32 (1.07 g, Yield 41%). $^1$H NMR (300 MHz, CDCl$_3$) analytical results of the product were as follows:

$^1$H NMR (300 MHz, CDCl$_3$): □ [ppm] 0.88 (m, 9H), 1.25-1.61 (m, 19H), 2.04 (m, 4H), 4.25 (t, 4H), 7.00 (d, 2H), 7.48 (d, 2H) 7.53 (d, 1H), 7.66 (s, 1H), 7.73 (d, 1H), 7.80-7.84 (m, 3H), 7.88 (s, 1H), 8.19 (d, 2H), 9.57 (d, 1H), 9.87 (d, 1H), 11.33 (m, 2H).

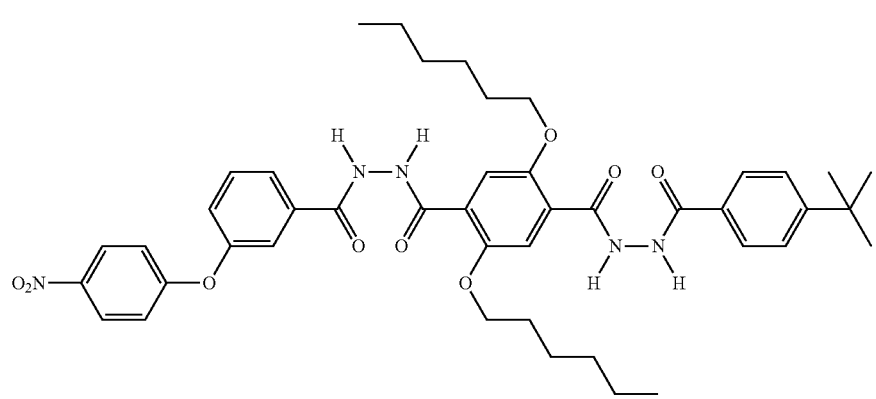

<Formula 32>

Synthesis Example 9

2-(2,5-bis(hexyloxy)-4-(5-(3-(4-nitrophenoxy)phenyl)-1,3,4-oxadiazole-2-yl)phenyl)-5-(4-t-butylphenyl)-1,3,4-oxadiazole 2.8 g of N'-1-(4-t-butylbenzoyl)-2,5-bis(hexyloxy)-N'-4-(3-(4-nitrophenoxy)benzoyl)terephthalohydrazide (3.7 mmol) prepared in Synthesis Example 8 was dissolved in 20 ml of phosphorus oxychloride ($POCl_3$), heated to 90□ and then reacted for 12 hours. The resultant product was cooled to room temperture, followed by adding excess iced water, neutralizing with sodium hydroxide, filtering and purifying by silica gel column chromatography (developed with a solution having ethyl acetate:n-hexane mixed in a ratio of 1:3) to yield a product having Formula 33 (1.1 g, Yield 38%). $^1$H NMR (300 MHz, $CDCl_3$) analytical results of the product were as follows:

$^1$H NMR (300 MHz, $CDCl_3$): □ [ppm] 0.85 (m, 9H), 1.32-1.42 (m, 18H), 1.91 (m, 4H), 4.25 (t, 4H), 7.08 (d, 2H), 7.32 (m, 1H), 7.54-7.66 (m, 2H), 7.76-7.91 (m, 3H), 8.02-8.10 (m, 2H), 8.23-8.28 (m, 4H).

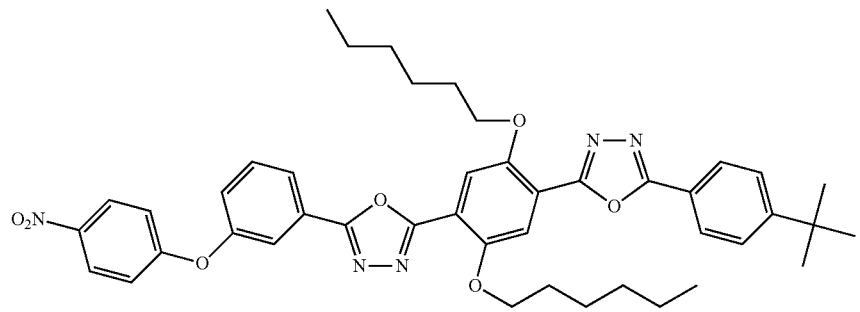

<Formula 33>

Synthesis Example 10

2-(5-(4-t-butylphenyl)-1,3,4-oxadiazole-2-yl)-5-(5-(3-(4-nitrophenoxy)phenyl)-1,3,4-oxadiazole-2-yl)benzene-1,4-diol 1.1 g of 2-(2,5-bis(hexyloxy)-4-(5-(3-(4-nitrophenoxy)phenyl)-1,3,4-oxadiazole-2-yl)phenyl)-5-(4-t-butylphenyl)-1,3,4-oxadiazole (1.44 mmol) prepared in Synthesis Example 9 was dissolved in 60 ml of dichloromethane at −78□, and 5 ml of boron tribromide was added thereto, followed by slowly raising the temperature to 0□. Thereafter, the reaction was quenched by addition of methanol, followed by adding excess water. The resultant solution was neutralized with dichloromethane, filtered, and performing silica gel column chromatography (developed with trichloromethane) to yield a product having Formula 34 (0.69 g, Yield 80%). $^1$H NMR (300 MHz, $CDCl_3$) analytical results of the product were as follows:

$^1$H NMR (300 MHz, $CDCl_3$): □ [ppm] 1.39 (s, 9H), 7.11 (d, 2H), 7.33 (d, 1H), 7.58-7.69 (m, 5H), 7.89 (s, 1H), 8.04 (s, 1H), 8.07 (d, 2H), 8.27 (d, 2H), 9.79 (s, 1H), 9.91 (s, 1H).

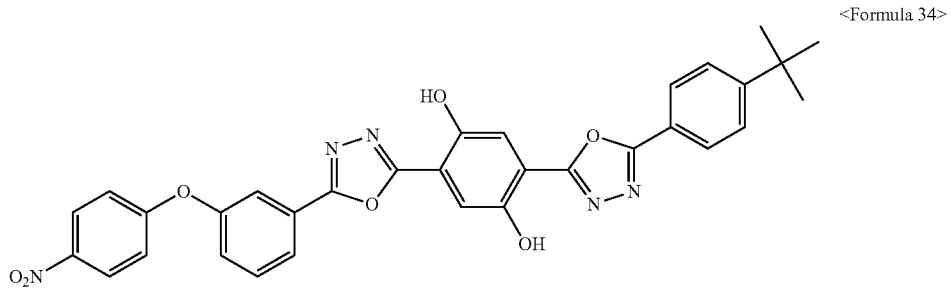 [SMILES: CC(C)(C)c1ccc(-c2nnc(-c3cc(O)c(-c4nnc(-c5cccc(Oc6ccc(N)cc6)c5)o4)cc3O)o2)cc1]

<Formula 34>

Synthesis Example 11

2-(5-(3-(4-aminophenoxy)phenyl)-1,3,4-oxadiazole-2-yl)-5-(5-(4-t-butylphenyl)-1,3,4-oxadiazole-2-yl)benzene-1,4-diol 0.69 g of 2-(5-(4-t-butylphenyl)-1,3,4-oxadiazole-2-yl)-5-(5-(3-(4-nitrophenoxy)phenyl)-1,3,4-oxadiazole-2-yl)benzene-1,4-diol prepared in Synthesis Example 10 was dissolved in 150 ml of THF, and 0.05 g of a catalyst having 5 wt % of palladium impregnated in activated carbon was added thereto. Gases generated in the solution by purging an argon (Ar) gas were removed to create a vacuum, followed by stirring for 18 hours while supplying $H_2$ gas (approximately 2-3 atm) for inducing a reaction. After the reaction was completed, the reaction product was filtered with Celite powder to remove the catalyst, and performing silica gel column chromatography (developed with a solution having ethylacetate: n-hexane mixed in a ratio of 1:2) to yield a product having Formula 35 (0.20 g, Yield 30%). IU NMR (300 MHz, $CDCl_3$) analytical results of the product were as follows:

$^1$H NMR (300 MHz, $CDCl_3$): [ppm] 1.26 (s, 9H), 3.75 (s, 2H), 6.70 (d, 2H), 6.90 (d, 2H), 7.08 (d, 1H), 7.42 (t, 1H), 7.53 (d, 2H), 7.72-7.83 (m, 4H), 8.06 (d, 2H).

Synthesis Example 12

2-(5-(4-t-butylphenyl)-1,3,4-oxadiazole-2-yl)-5-(5-(3-(4-(2-(2-hydroxyphenyl)-4,5-diphenyl-1H-imidazole-1-yl)phenoxy)phenyl)-1,3,4-oxadiazole-2-yl)benzene-1,4-diol 0.11 g of benzyl (0.53 mmol) and 0.07 ml of salicylic aldehyde (0.59 mmol) were added in 120 ml of iced acetic acid at room temperature, and 0.30 g of 2-(5-(3-(4-aminophenoxy)phenyl)-1,3,4-oxadiazole-2-yl)-5-(5-(4-t-butylphenyl)-1,3,4-oxadiazole-2-yl)benzene-1,4-diol (0.53 mmol) prepared in Synthesis Example 11 was added thereto, followed by adding 0.41 g of ammonium acetate (5.3 mmol) thereto, heating to 110□ and reacting for 12 hours. After the reaction was completed, the resultant product was reprecipitated with cyclohexane, recrystallized with an ethylacetate solution to yield a product having Formula 22 (0.15 g, Yield 32%). $^1$H NMR (300 MHz, $CDCl_3$) analytical results of the product were as follows:

$^1$H NMR (300 MHz, $CDCl_3$): □ [ppm] 1.42 (s, 9H), 6.63-6.70 (m, 2H), 7.05-7.12 (m, 3H), 7.18-7.36 (m, 12H), 7.56-7.70 (m, 6H), 7.82 (s, 1H), 7.95 (d, 1H), 8.10 (d, 2H), 9.86 (s, 1H), 9.5 (s, 1H), 13.39 (s, 2H).

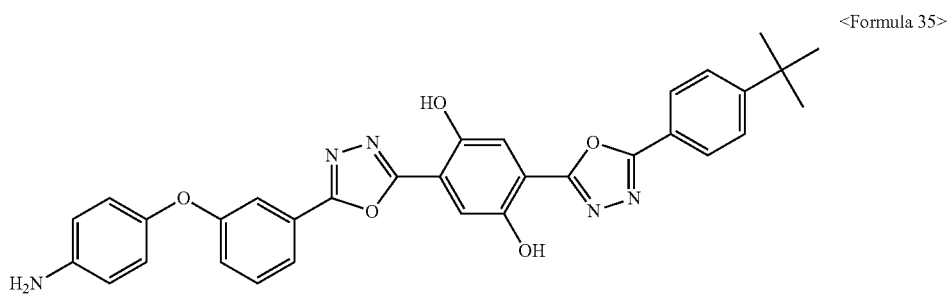

<Formula 35>

<Formula 22>

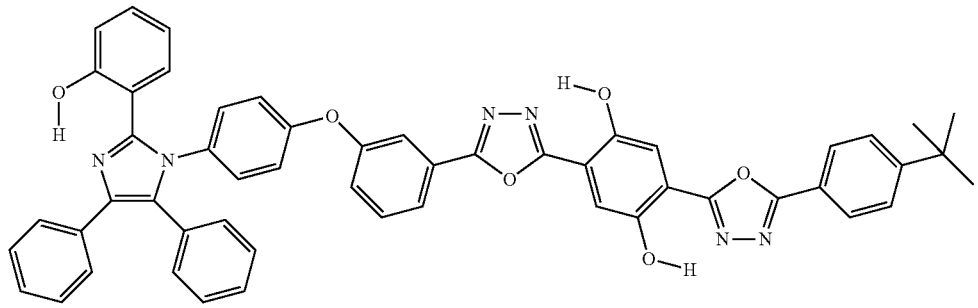

Synthesis Example 13

2,5-bis(hexyloxy)-N'1,N'4-bis(3-(4-nitrophenoxy)benzoyl)terephthalohydrazide 1.65 g of 2,5-bis(hexyloxy)terephthaloyl dichloride (4.1 mmol) prepared in Synthesis Example 7 was dissolved in 120 ml of THF at room temperature, and then added thereto a solution prepared by dissolving 2.24 g of 3-(4-nitrophenoxy)benzohydrazide (8.2 mmol) prepared in Synthesis Example 3 in 50 ml of THF, followed by stirring 12 hours for inducing a reaction. After the reaction was completed, THF was removed under reduced pressure, followed by performing silica gel column chromatography (developed with a solution having ethylacetate:n-hexane mixed in a ratio of 1:3) to yield a product having Formula 36 (2.7 g, Yield 75%). $^1$H NMR (300 MHz, CDCl$_3$) analytical results of the product were as follows:

$^1$H NMR (300 MHz, CDCl$_3$): □ [ppm] 0.88 (t, 6H), 1.33-1.58 (m, 16H), 4.25 (t, 4H), 7.03 (d, 4H), 7.30 (d, 2H), 7.55 (d, 2H), 7.65 (s, 2H), 7.71 (d, 2H), 7.85 (d, 2H), 8.21 (d, 4H), 9.71 (d, 2H), 11.29 (d, 2H).

Synthesis Example 14

5,5'-(2,5-bis(hexyloxy)-1,4-phenylene)bis(2-(3-(4-nitrophenoxy)phenyl)-1,3,4-oxadiazole)

2.7 g of 2,5-bis(hexyloxy)-N'1,N'4-bis(3-(4-nitrophenoxy)benzoyl)terephthalohydrazide (3.1 mmol) prepared in Synthesis Example 13 was dissolved in 20 ml of phosphorus oxychloride (POCl$_3$), heated to 90□ and then reacted for 12 hours. The resultant product was cooled to room tempreture, followed by adding excess iced water, neutralizing with sodium hydroxide, filtering and performing silica gel column chromatography (developed with a solution having ethyl acetate:n-hexane mixed in a ratio of 1:1) to yield a product having Formula 37 (0.9 g, Yield 30%). XH NMR (300 MHz, CDCl$_3$) analytical results of the product were as follows:

$^1$HNMR (300 MHz, CDCl$_3$): [ppm] 0.82-0.91 (m, 6H), 1.25-1.51 (m, 16H), 4.16 (m, 4H), 7.05 (d, 4H), 7.31 (d, 2H), 7.61 (t, 2H), 7.83 (s, 2H), 7.89 (s, 2H), 8.04 (s, 2H), 8.25 (d, 4H).

<Formula 36>

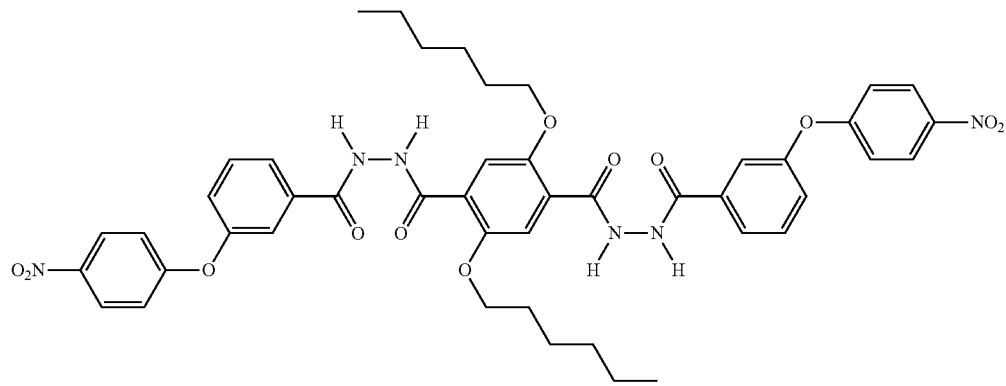

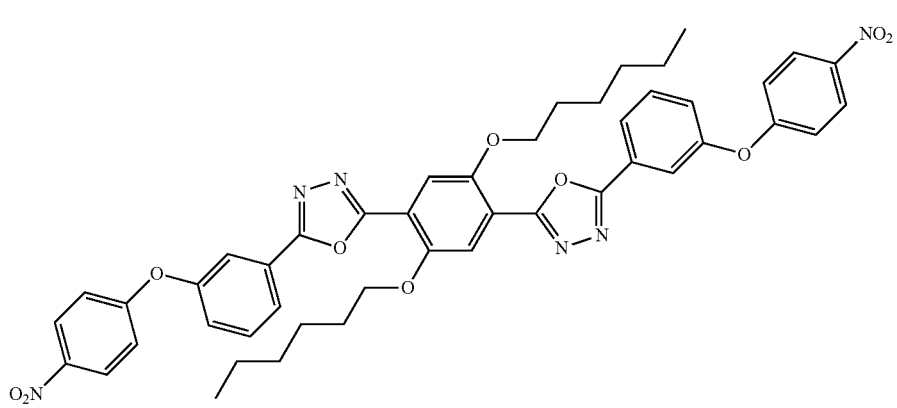

<Formula 37>

Synthesis Example 15

2,5-bis(5-(3-(4-nitrophenoxy)phenyl)-1,3,4-oxadiazole-2-yl)benzene-1,4-diol 3.04 g of 5,5'-(2,5-bis(hexyloxy)-1,4-phenylene)bis(2-(3-(4-nitrophenoxy)phenyl)-1,3,4-oxadiazole) (3.6 mmol) prepared in Synthesis Example 9 was dissolved in 120 ml of dichloromethane at −78□, and 3.5 ml of boron tribromide (35.6 mmol) was added thereto, followed by slowly raising the temperature to 0□. Thereafter, the reaction was quenched by addition of methanol, followed by adding excess water. The resultant solution was neutralized with dichloromethane, filtered, and performing silica gel column chromatography (developed with trichloromethane) to yield 0.4 g of a product having Formula 38. $^1$H NMR (300 MHz, CDCl$_3$) analytical results of the product were as follows:

$^1$H NMR (300 MHz, CDCl$_3$) □ [ppm] 7.10 (d, 4H), 7.34 (d, 2H), 7.63 (s, 2H), 7.69 (d, 2H), 7.89 (s, 2H), 8.07 (d, 2H), 8.26 (d, 4H) 12.04 (s, 2H).

Synthesis Example 16

2,5-bis(5-(3-(4-aminophenoxy)phenyl)-1,3,4-oxadiazole-2-yl)benzene-1,4-diol 0.30 g of 2,5-bis(5-(3-(4-nitrophenoxy)phenyl)-1,3,4-oxadiazole-2-yl)benzene-1,4-diol prepared in Synthesis Example 15 was dissolved in 150 ml of THF, and 0.05 g of a catalyst having 5 wt % of palladium impregnated in activated carbon was added thereto. Gases generated in the solution by purging an argon (Ar) gas were removed to create a vacuum, followed by stirring for 18 hours while supplying H$_2$ gas (approximately 2-3 atm) for inducing a reaction. After the reaction was completed, the reaction product was filtered with Celite powder to remove the catalyst, and performing silica gel column chromatography (developed with a solution having ethylacetate:n-hexane mixed in a ratio of 1:2) to yield 0.1 g of a product having Formula 39. $^1$H NMR (300 MHz, CDCl$_3$) analytical results of the product were as follows:

$^1$H NMR (300 MHz, CDCl$_3$) □ [ppm] 4.93 (s, 4H), 6.48-7.19 (m, 10H), 7.34-7.60 (m, 4H), 7.68-7.98 (m, 6H).

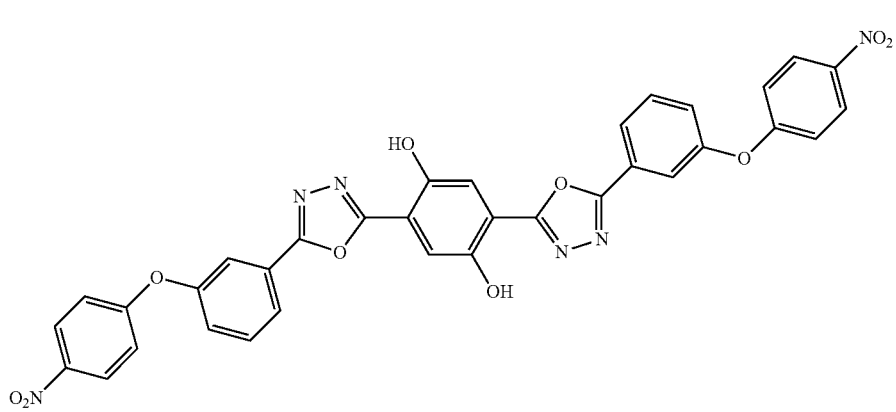

<Formula 38>

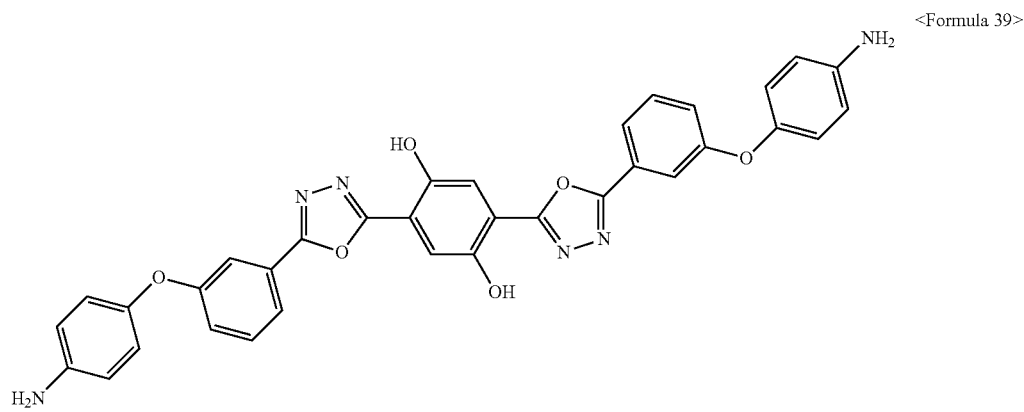 [SMILES: O=[N+]([O-])c1ccc(Oc2cccc(-c3nnc(-c4cc(O)c(-c5nnc(-c6cccc(Oc7ccc([N+](=O)[O-])cc7)c6)o5)cc4O)o3)c2)cc1]
<Formula 39>

Synthesis Example 17

2,5-bis(5-(3-(4-(2-(2-hydroxyphenyl)-4,5-diphenyl-1H-imidazole-1-yl)phenoxy)phenyl)-1,3,4-oxadiazole-2-yl)benzene-1,4-diol 0.15 g of benzyl (0.72 mmol) and 0.08 ml of salicylic aldehyde (0.72 mmol) were added in 120 ml of iced acetic acid at room temperature, and 0.20 g of 2,5-bis(5-(3-(4-aminophenoxy)phenyl)-1,3,4-oxadiazole-2-yl)benzene-1,4-diol (0.33 mmol) prepared in Synthesis Example 16 was added thereto, followed by adding 0.50 g of ammonium acetate (6.6 mmol) thereto, heating to HOD and reacting for 12 hours. After the reaction was completed, excess water was added to the resultant product and reprecipitated with cyclohexane, recrystallized with an ethylacetate solution to yield a product having Formula 24 (0.012 g, Yield 3.0%). $^1$H NMR (300 MHz, CDCl$_3$) analytical results of the product were as follows:

$^1$H NMR (300 MHz, CDCl$_3$) □ [ppm] 6.91 (m, 2H), 6.98-7.06 (m, 6H), 7.10-7.24 (m, 20H), 7.32-7.36 (m, 2H), 7.41-7.53 (m, 8H), 7.74-7.87 (m, 8H), 12.02-12.10 (m, 4H)

Synthesis Example 18
N-(4-(4-(2-(2-hydroxy-phenyl)-4,5-diphenyl-1H-imidazole-1-yl)phenoxy)phenyl)acetamide 4.199 g of benzyl (19.97 mmol) and 2.14 ml of salicylic aldehyde (19.97 mmol) were added in 120 ml of iced acetic acid at room temperature, and 4.00 g 4,4'-oxydianiline (19.97 mmol) was dropwise added thereto, followed by adding 7.70 g of ammonium acetate (99.8 mmol) thereto, heating to HOD and reacting for 12 hours. After the reaction was completed, excess water was added to the resultant product and performing silica gel column chromatography (developed with a solution having ethyl acetate:n-hexane mixed in a ratio of 1:3) to yield a product having Formula 40 (5.05 g, Yield 47%). XH NMR (300 MHz, CDCl$_3$) analytical results of the product were as follows:

$^1$H NMR (300 MHz, CDCl$_3$) □ [ppm] 2.18 (s, 3H), 6.53 (t, 1H), 6.64 (d, 1H), 6.92-6.97 (m, 4H), 7.06-7.24 (m, 10H), 7.28-7.33 (m, 3H), 7.48-7.55 (m, 4H), 13.44 (s, 1H).

<Formula 24>
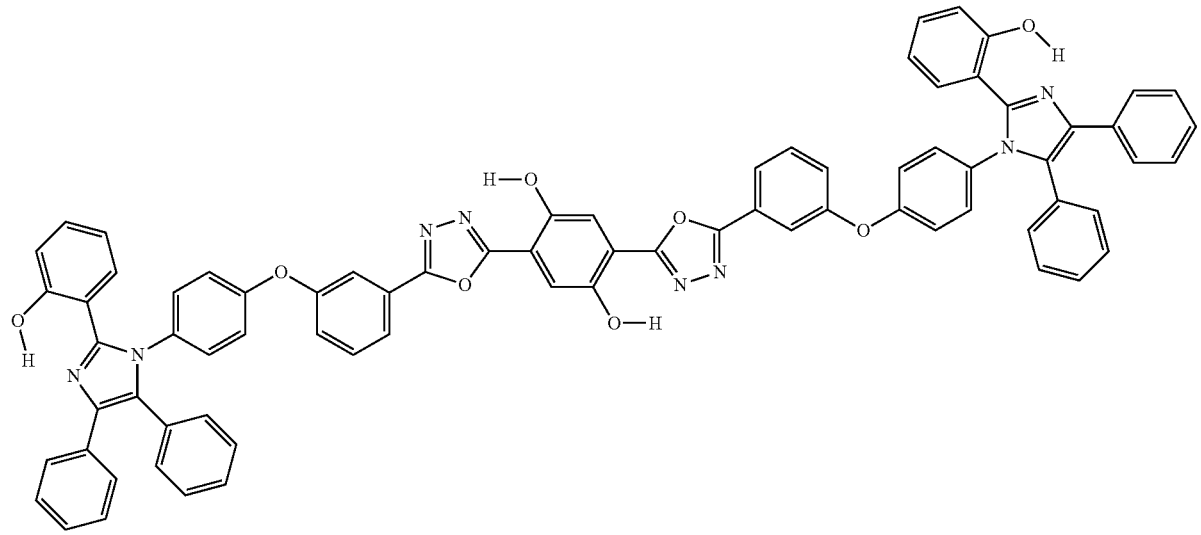

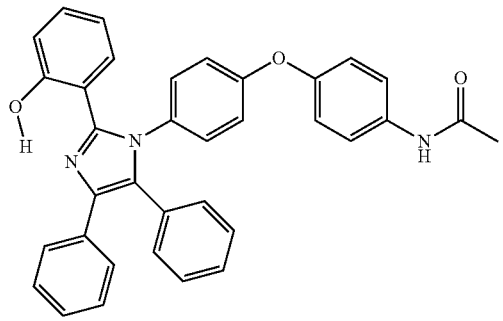

<Formula 40>

Synthesis Example 19

2-(1-(4-(4-aminophenoxy)phenyl)-4,5-diphenyl-1H-imidazole-2-yl)phenol

To 100 ml of a solution prepared by mixing EtOH and water in a volume ratio of 1:1 was added 3.0 g of N-(4-(4-(2-(2-hydroxyphenyl)-4,5-diphenyl-1H-imidazole-1-yl)phenoxy)phenyl)acetamide prepared in Synthesis Example 18, and 15 ml of hydrochloric acid (37%) was added thereto, and reacted under reflux at 100□ for 12 hours. After the reaction was completed, excess water was added to the resultant product, and the resultant product was neutralized with potassium carbonate, filtered, dried and performing silica gel column chromatography (developed with a solution having ethylacetate:n-hexane mixed in a ratio of 1:3) to yield a product having Formula 41 (2.59 g, Yield 94%). XH NMR (300 MHz, CDCl$_3$) analytical results of the product were as follows:

$^1$H NMR (300 MHz, CDCl$_3$□□□ [ppm] 3.73 (d, 2H), 6.51 (t, 1H), 6.64 (d, 1H), 6.70 (d, 2H), 6.83-6.90 (m, 4H), 7.05-7.14 (m, 3H), 7.15-7.23 (m, 6H), 7.27-7.31 (m, 4H), 7.51 (d, 2H)

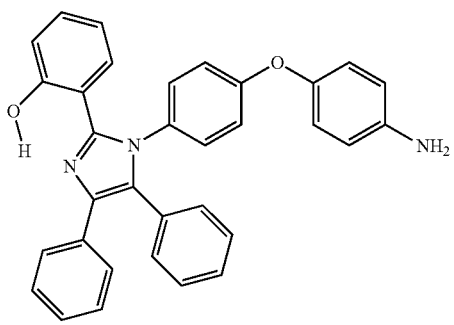

<Formula 41>

Synthesis Example 20

3-hydroxy-2 naphthaldehyde (3-hydroxy-2-naphthaldehyde)

4.64 g of 2-naphthol (32.2 mmol) was dissolved in 20 ml of THF, and 43 ml of a 1.7 M t-butyltin solution (72.4 mmol) prepared by dissolving t-butyltin in penthane was dropwise added thereto for 2 minutes. The generated gases were removed and reacted for further 4 hours. Thereafter, the reaction product was cooled to 0□, and a solution prepared by adding 12 ml of dimethylformamide to 16 ml of THF was added thereto and reacted by stirring at room temperature for 24 hours. An extract was obtained using ethyl acetate and performing silica gel column chromatography (developed with a solution having ethylacetate:n-hexane mixed in a ratio of 1:3) to yield a product having Formula 42 (0.62 g, Yield 6%). The melting point of the product was 100-102□ and IR (KBr) and XH NMR (300 MHz, CDCl$_3$) analytical results of the product were as follows:

IR (KBr) 3390, 3040, 2960, 1665, 1495, 1455, 1380, 1110, 880, 745 cm$^{-1}$ $^1$H NMR (300 MHz, CDCl$_3$): □ [ppm] 7.29 (s, 1H), 7.35 (t, 1H), 7.54 (t, 1H), 7.70 (d, 1H), 7.86 (d, 1H), 8.16 (s, 1H), 10.09 (s, 1H), 10.31 (s, 1H).

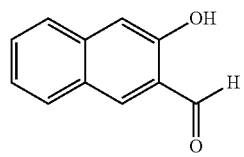

<Formula 42>

Synthesis Example 21

3-(1-(4-(4-(2-(2-hydroxyphenyl)-4,5-diphenyl-1H-imidazole-1-yl)phenoxy)phenyl)-4,5-diphenyl-1H-imidazole-2-yl)naphthalene-2-ol 0.30 g of 3-hydroxy-2-naphthaldehyde (1.74 mmol) prepared in Synthesis Example 20 was dissolved in 100 ml of acetic acid, and 0.86 g of 2-(1-(4-(4-aminophenoxy)phenyl)-4,5-diphenyl-1H-imidazole-2-yl)phenol (1.74 mmol) prepared in Synthesis Example 19, 0.37 g of benzyl (1.74 mmol) and 0.94 g of ammonium acetate (12.2 mmol) were added thereto, followed by heating to HOD and reacting for 12 hours. Thereafter, excess water was added to the resultant product and performing silica gel column chromatography (developed with a solution having ethylacetate:n-hexane mixed in a ratio of 1:3) to yield a product having Formula 18 (0.67 g, Yield 45%). XH NMR (300 MHz, CDCl$_3$) and $^{13}$C NMR (500 MHz, CDCl$_3$) analytical results of the product were as follows:

$^1$H NMR (300 MHz, CDCl$_3$): □ [ppm] 6.48 (t, 1H), 6.62 (d, 1H), 6.96-7.02 (m, 4H), 7.10-7.24 (m, 13H), 7.27-7.42 (m, 11H), 7.52-7.66 (m, 6H), 13.09 (s, 1H), 13.36 (s, 1H).

$^{13}$C NMR (500 MHz, CDCl$_3$): [ppm] 110.05, 111.45, 113.75, 116.38, 116.44, 118.06, 118.54, 121.71, 124.39, 124.53, 125.20, 125.29, 125.42, 125.50, 125.64, 125.78, 126.42, 126.84, 126.89, 127.09, 127.16, 128.17, 128.32, 128.60, 128.89, 128.98, 129.89, 131.38, 131.47, 133.18, 134.54, 143.05, 143.56, 153.78, 153.32, 157.02.

<Formula 18>

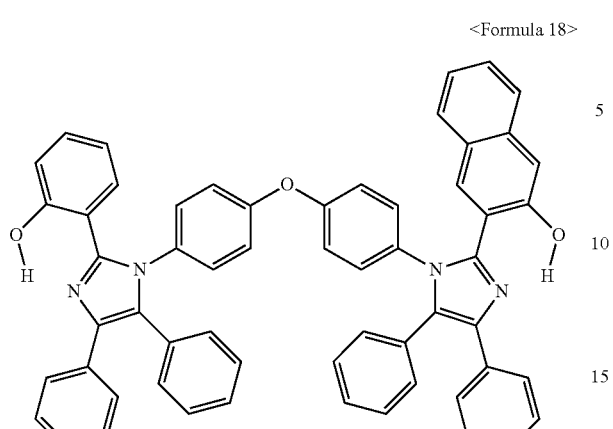

Example 1

Figure 4:
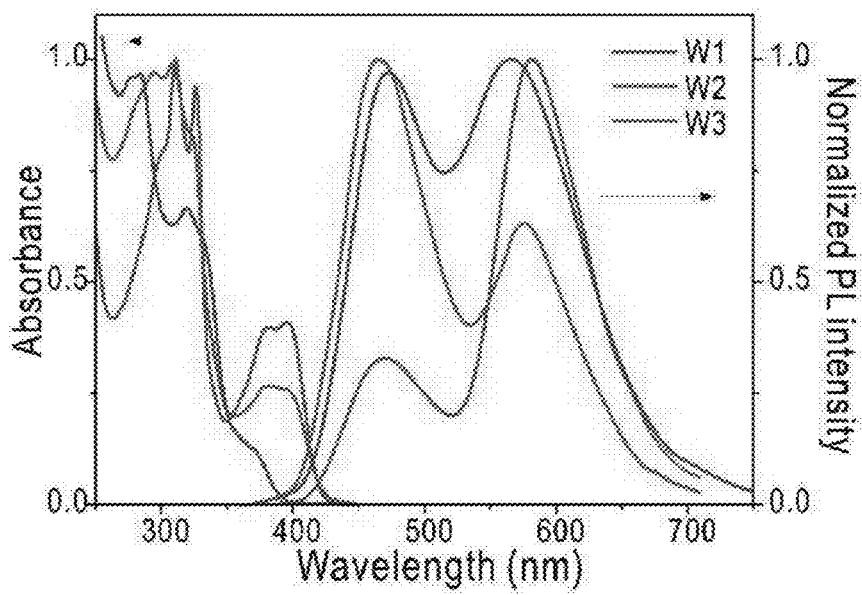
FIG. 4 illustrates photoluminescence (PL) spectral analysis results of white-emitting monomolecular compounds according to the present invention.
Figure 6:
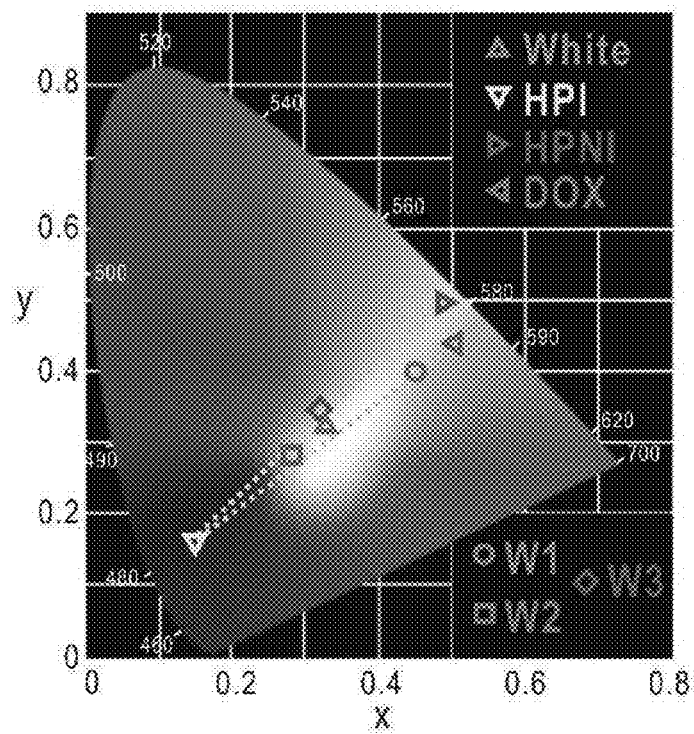
FIG. 6 illustrates CIE color coordinates of a white-emitting monomolecular compound according to the present invention and the conventional ESIPT monomolecules, as measured in Example 1.

A film was formed on a glass substrate by doping 6 wt % of the compound (W1) of Formula 22 prepared in Synthesis Example 12, the compound (W2) of Formula 24 prepared in Synthesis Example 17, and the compound (W3) of Formula 18 prepared in Synthesis Example 21. Photo luminescence (PL) spectral analysis was performed on the film, and the PL analytical result is shown in FIG. 4 and the CIE color coordinate is shown in FIG. 6. The PL analysis was performed using a 325 nm He—Cd laser as a light source and a GaAs detector with quantum efficiency in the 300-900-nm spectral range as a photodetector.

Figure 5:
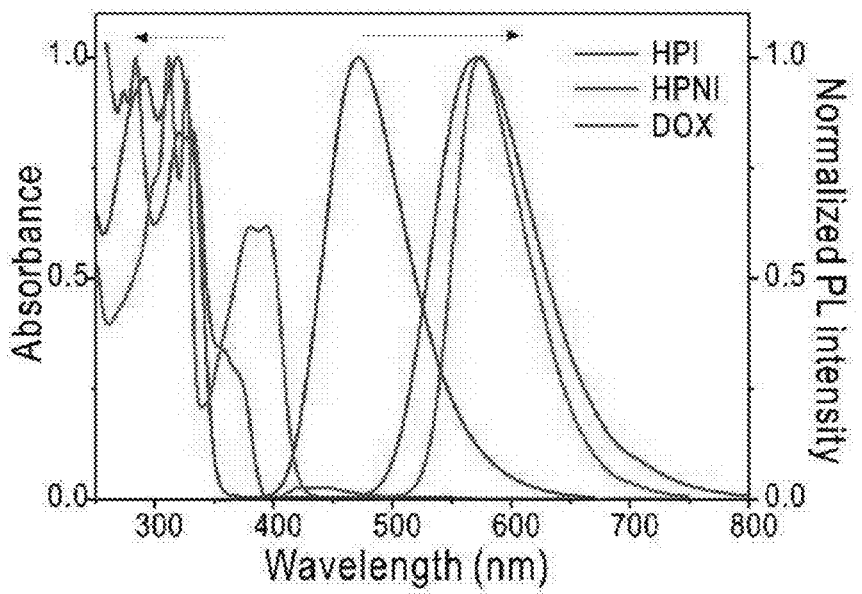
FIG. 5 illustrates photoluminescence (PL) spectral analysis results of conventional ESIPT monomolecular as measured in Example 1.

To compare the PL analytical results of the white-emitting monomolecular compounds according to the present invention and the conventional ESIPT molecules, 2-(1,4,5-triphenyl-1H-imidazole-2-yl)phenol (HPI, $\lambda_{max}$=460 nm), 5-bis(5-(4-tert-butylphenyl)-1,3,4-oxadiazole-2-yl)benzene-1,4-diol (DOX, $\lambda_{max}$=580 nm) and 3-(1,4,5-triphenyl-1H-imidazole-2-yl)naphthalene-2-ol (HPNI, $\lambda_{max}$=580 nm) were doped to be contained in polystylene each in an amount of 6 wt %, forming films. The PL spectral anaysis was performed on the films. The PL analytical results for the conventional ESIPT molecules, that is, HPI, HPNI and DOX, are shown in FIG. 5 and the CIE color coordinates thereof are shown in FIG. 6.

As shown in FIG. 4, the compounds W1, W2, and W3 synthesized according to the present invention showed absorbance peaks at 347, 320, and 330 nm. As shown in FIG. 6, based on the color coordinate (0.33, 0.33), as indicated by symbol A, showing ideal white luminescence, the color coordinates of the compounds W1, W2 and W3, as indicated by symbols ○, □, and ◇, were (0.45, 0.40), (0.28, 0.29), and (0.33, 0.37), respectively, confirming efficient white luminescence. This is presyambly because the white-emitting monomolecular compounds according to the present invention prepared by covalently bonding two or more ESIPT molecules developing different colors could prevent the energy transfer by completely restricting an interaction between an energy acceptor and an energy donor.

Example 2

To confirm luminescence intensity depending on changes in the concentrations of the white-emitting monomolecular compounds according to the present invention, for example, the compound W3, was added to $CHCl_3$ while varying its concentrations, that is, $1 \times 10^{-3}$M, $1 \times 10^{-4}$ M and $1 \times 10^{-5}$M, and PL spectral analysis was performed thereon. The PL spectral analysis results are shown in FIG. 7.

Figure 7:
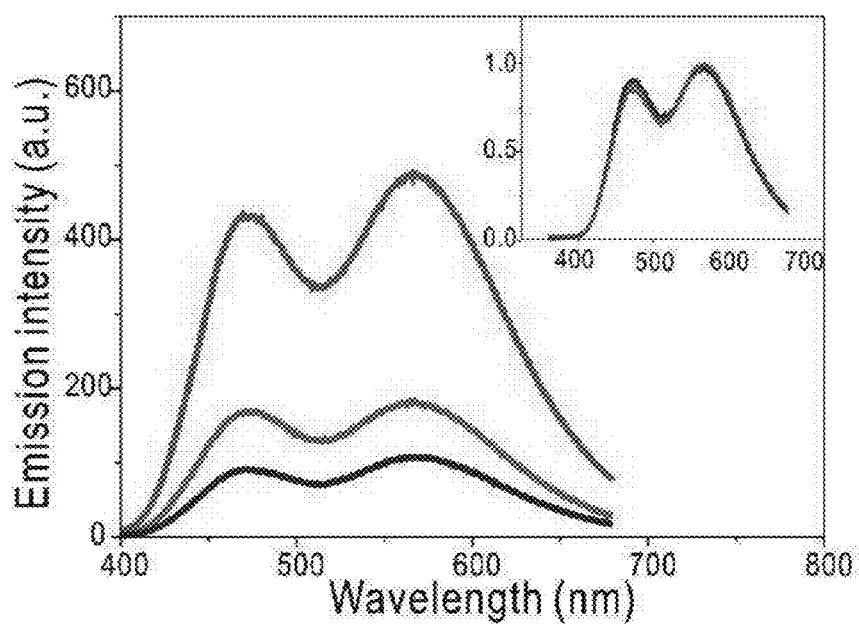
FIG. 7 illustrates emission intensity depending on the change in the concentration of a white-emitting monomolecular compound in Example 2 of the present invention.

As confirmed from FIG. 7, the PL intensity of the white-emitting monomolecular compound according to the present invention, that is, the compound W3, could be adjusted by varying its concentration.

Example 3

Each of the conventional ESIPT molecules HPI, W3 and HPNI was added to $CHCl_3$ in a concentration $1 \times 10^{-5}$ M, and then thinly dispersed on a glass substrate, followed by UV lamp irradiation using a 365 nm UV lamp. The UV lamp irradiation results are shown in FIG. 8.

Figure 8:
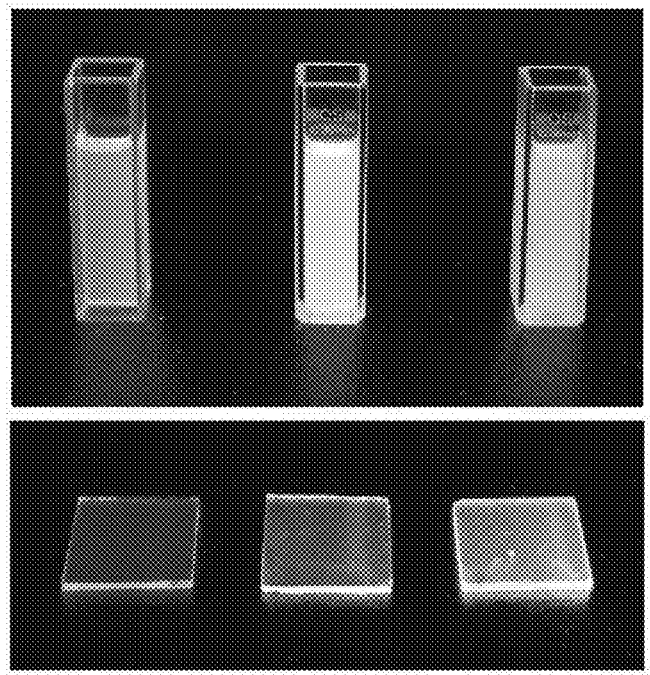
FIG. 8 illustrates UV lamp irradiation results for white-emitting monomolecular compounds in Example 3.

As confirmed from FIG. 8, the white-emitting monomolecular compound according to the present invention, that is, the compound W3, showed efficient white luminescence.

Example 4

Figure 9:
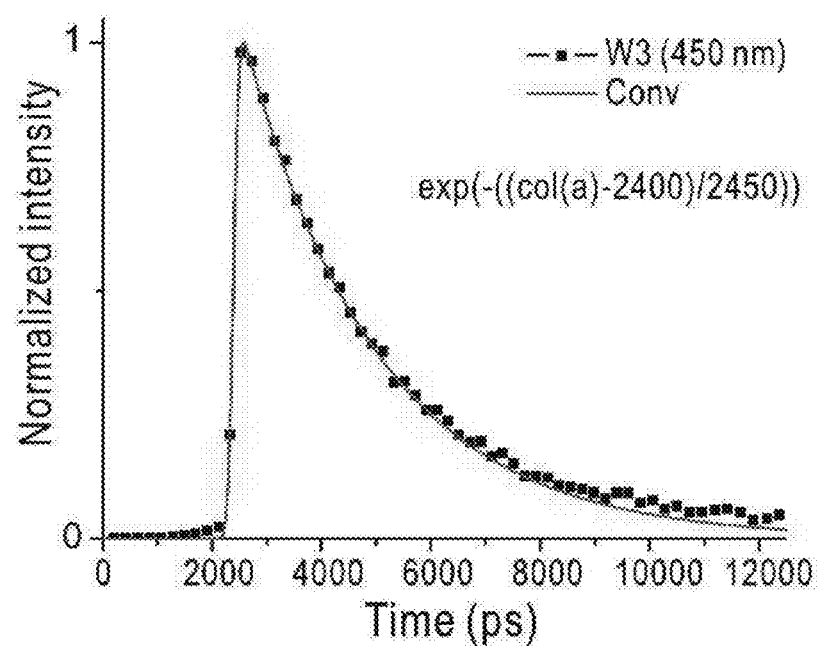
FIGS. 9 and 10 illustrate normalized intensities of a white-emitting monomolecular compound having Formula 18 in Example 4 of the present invention over time (ps) in 450 nm and 690 nm, respectively.
Figure 10:
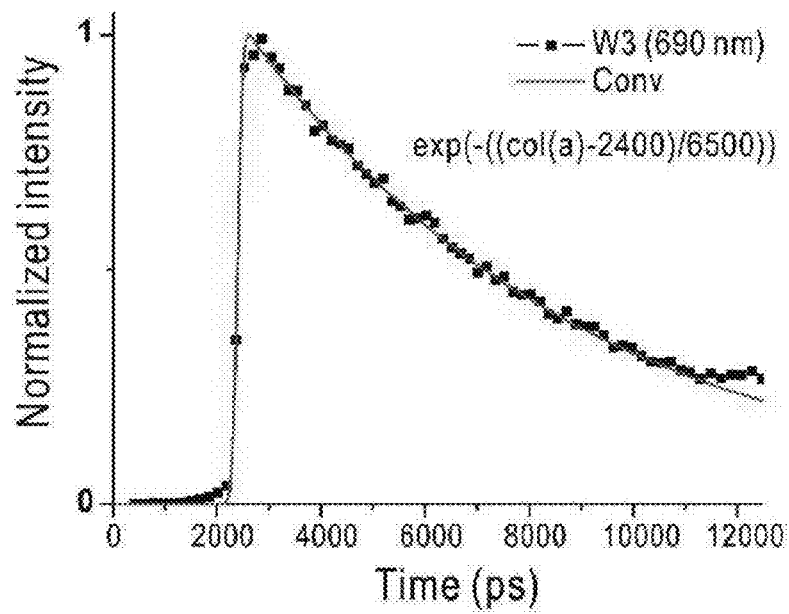

A film was formed on a glass substrate by doping 6 wt % of the compound W3 having Formula 18 prepared in Synthesis Example 21 into polystylene. The film was exposed to absorption intensity of 347 nm, and normalized PL intensities were measured over time at 450 nm and 690 nm, respectively. The measurement results are shown in FIGS. 9 and 10.

Figure 11:
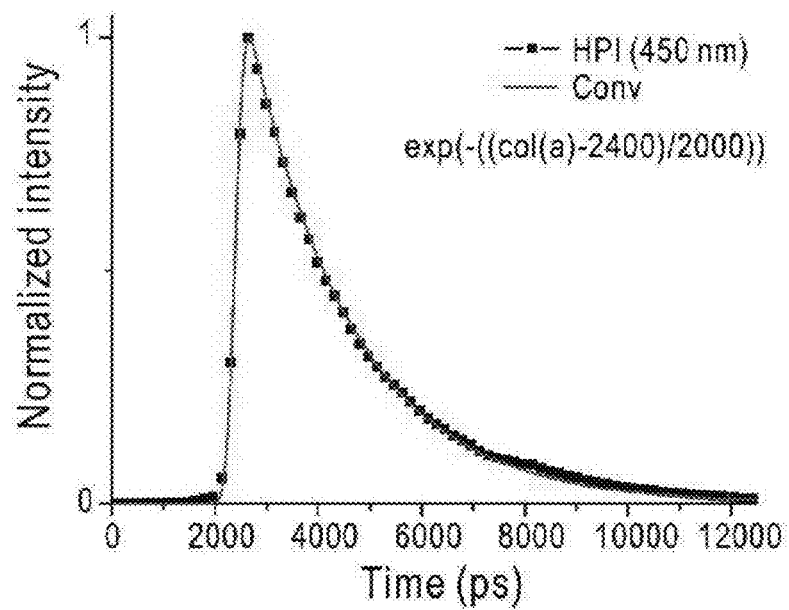
FIGS. 11 and 12 illustrate the intensity normalized per unit time of a conventional ESIPT monomolecular compound, as measured in Example 4.
Figure 12:
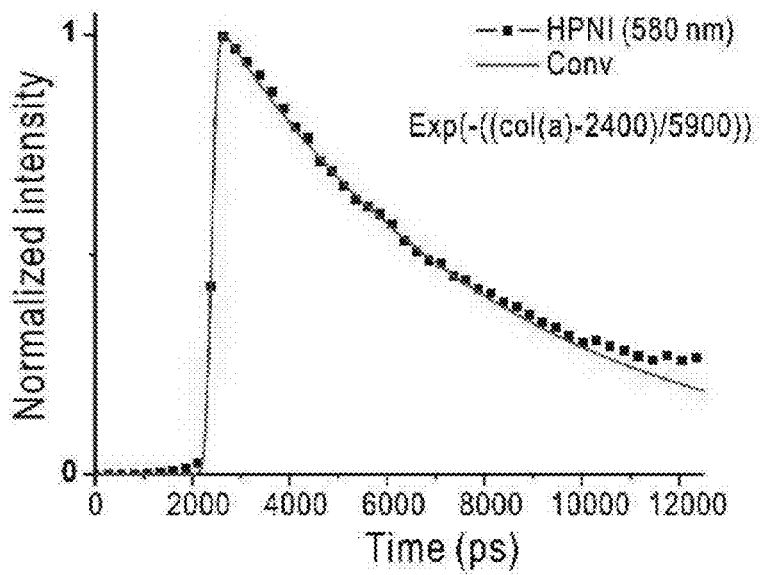

To compare the PL intensity of the compound W3 with that of the conventional ESIPT monomolecule, a film was formed by doping 6 wt % of each of HPI and HPNI into polystylene. Each film was exposed to absorption intensity of 347 nm, and the normalized PL intensities for HPI and HPNI were measured over time at 450 nm and 690 nm, respectively. The measurement results are shown in FIGS. 11 and 12.

As shown in FIGS. 9 through 12, the white-emitting monomolecular compound according to the present invention, that is, the compound W3, exhibited substantially the same PL intensity with HPI and HPNI.

Experimental Example 1

Fabrication and Evaluation of White Organic Electroluminescent Element

A glass substrate having a 25 mm×25 mm×1.1 mm indium tin oxide (ITO) transparent electrode was subjected to ultrasonic cleaning for 5 minutes, followed by UV ozone cleaning for 30 minutes. The cleaned glass substrate having the transparent electrode was mounted on a substrate holder of a vacuum deposition device, and 4,4'-bis[N-(1-naphthyl)-N-phenyl-amino]-biphenyl (NPD) as a hole transport material was deposited on a surface of the glass substrate having the transparent electrode to a thickness of 40 nm, forming a film, and the compound W3 of Formula 18 prepared in Synthesis Example 21 was formed thereon to a thickness of 30 nm. Thereafter, 4,7-diphenyl-1,10-phenantroline (Bphen) as an electron transporting material was formed into a film having a thickness of 50 nm, and an Li layer was formed thereon to a thickness 1 nm at a rate of 0.1 Å/sec, followed by depositing Al on the Li film to form an electrode having a thickness of 100 nm, thereby fabricating an organic electroluminescent element. During deposition, deposition equipment (Sunicel plus 200) manufactured by Sunic System Ltd. of Korea was used.

The efficiency of the fabricated OLED was measured using a Photo Research PR650 spectrometer, and the I-V characteristic of the fabricated OLED was measured using a Keithley 236 source measure unit. The measurement results are shown in Table 1 and the wavelength dependent PL intensity is shown in FIG. 13.

TABLE 1

| (at 10 mA/cm$^2$) | Driving voltage [V] | Luminance [cd/m$^2$] | Efficiency [cd/A] | Color coordinates |
|---|---|---|---|---|
| Experimental Example 1 | 9.71 | 97 | 0.97 | 0.343, 0.291 |

Figure 13:
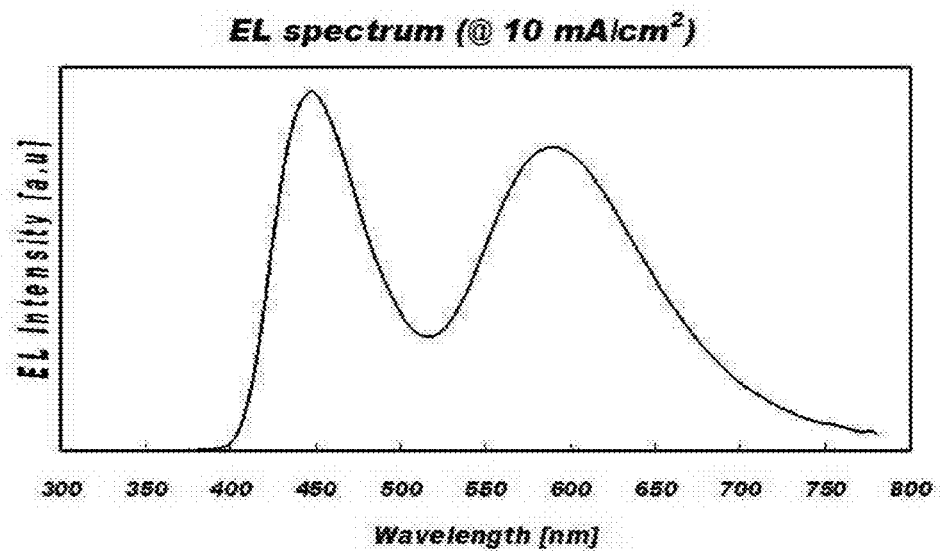
FIG. 13 illustrates the EL spectrum of an organic electroluminescent element fabricated using a white-emitting monomolecular compound having Formula 18 prepared in Experimental Example 1 of the present invention.

As confirmed from Table 1 and FIG. 13, when the white-emitting monomolecular compound according to the present invention is applied to an OLED, efficient white luminescence can be achieved.

Experimental Example 2

Application of the Inventive Compound to a Laser Device

Figure 14:
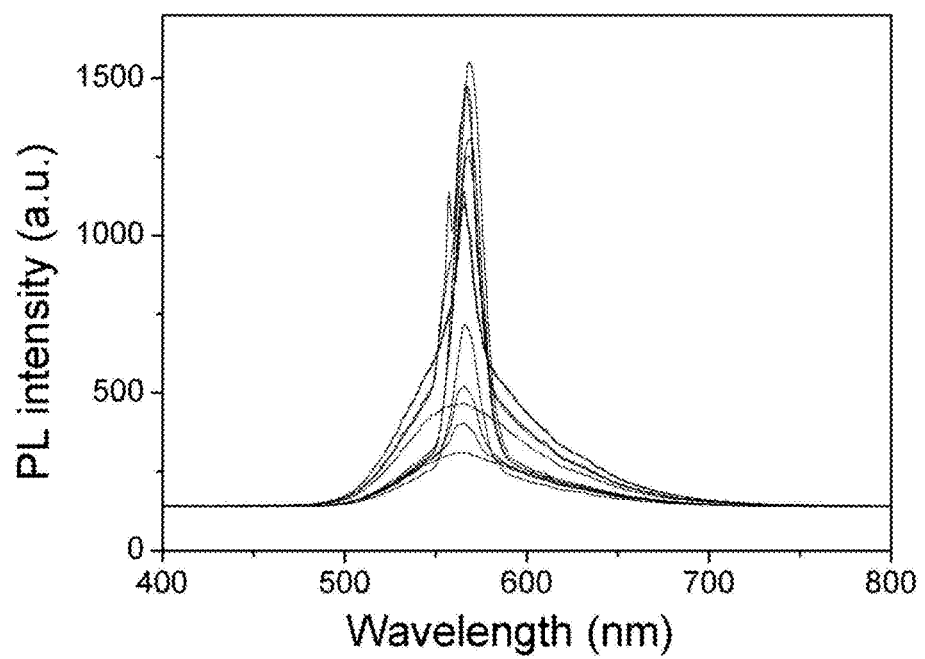
FIG. 14 illustrates the PL intensity dependent EL spectral changes of a white-emitting monomolecular compound having Formula 18 prepared in Experimental Example 2.

The compound W3 having Formula 18 prepared in Synthesis Example 21 was allowed to grow in ethylacetate into single crystals, and pulse-excited emission spectra were measured using an actively/passively mode-locked 355 nm Nd:YAG Laser (Quantel, YG701). By optically pumping, amplified spontaneous emission (ASE), also known as mirrorless lasing, was observed, and the results are shown in FIG. 14. Here, Spectrapro-500 manufactured by Acton Research Corp. was used to observe the ASE.

Although exemplary embodiments of the present invention have been described in detail hereinabove, it should be understood that many variations and modifications of the basic inventive concept herein described, which may appear to those skilled in the art, will still fall within the spirit and scope of the exemplary embodiments of the present invention as defined by the appended claims.

What is claimed is:

1. A white-emitting monomolecular compound represented by Formula 23:

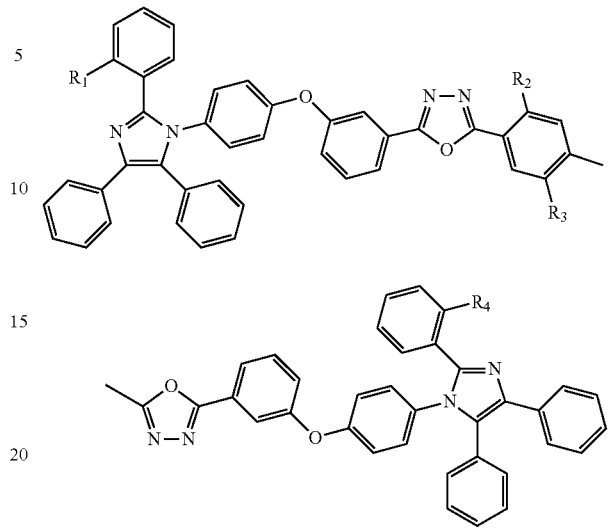

<Formula 23> wherein $R_2$, $R_3$, and R4 are each independently selected from the group consisting of a hydrogen atom, a hydroxy group, a linear, branched or cyclic C1-C20 alkyl group, a C1-C20 alkoxy group, a substituted or unsubstituted C1-C20 carbonyl group, an aryloxy group substituted with an aromatic or cyclic compound, a halogen atom, a trifluoromethyl group, a C1-C20 sulfonic group substituted with an alkyl group, a sulfonic group substituted with an aromatic cyclic compound or an aryl group, a C1-C20 substituted alkylamide group, an arylamide group substituted with an aromatic cyclic compound or an aryl group, an amino group, a nitro group, a cyano group, a sulfone amide group, a thiol group, and a fluorous acid group, which contain hydrogen capable of forming a hydrogen bond with a nitrogen atom of an adjacent ring; and $R_1$ is selected from the group consisting of a hydroxyl group, an amino group, an alkylamide group, an arylamide group, a sulfone amide group, a sulfonic group substituted with an aromatic cyclic compound or an aryl group, a thiol group, and a fluorous acid group, which contain hydrogen capable of forming a hydrogen bond with a nitrogen atom of an adjacent ring.

2. The white-emitting monomolecular compound of claim 1, wherein the white-emitting monomolecular compound is represented by Formula 24:

<Formula 24>

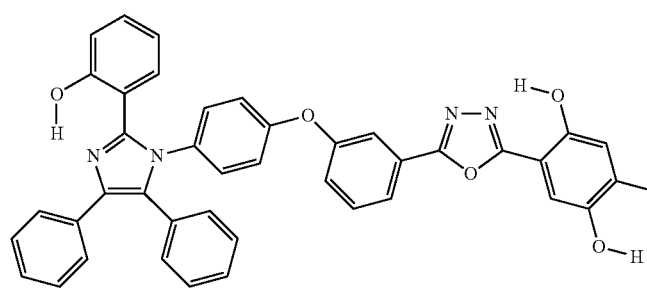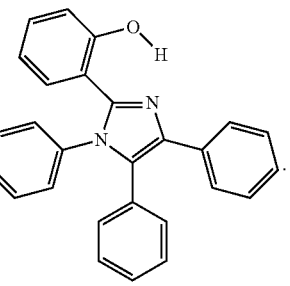

3. An organic electroluminescent element comprising the white-emitting monomolecular compound of claim 1.

4. A laser device including the white-emitting monomolecular compound of claim 1.

5. The organic electroluminescent element of claim 3, wherein the white-emitting monomolecular compound of claim 1 is represented by Formula 24.

6. The laser device of claim 4, wherein the white-emitting monomolecular compound of claim 1 is represented by Formula 24.

* * * * *